US008425844B2

(12) United States Patent
Willett et al.

(10) Patent No.: US 8,425,844 B2
(45) Date of Patent: Apr. 23, 2013

(54) DETECTION APPARATUS FOR BIOLOGICAL MATERIALS AND METHODS OF MAKING AND USING THE SAME

(75) Inventors: Robert L. Willett, Warren, NJ (US); Kirk W. Baldwin, Springfield, NJ (US); Loren N. Pfeiffer, Harding Township, NJ (US)

(73) Assignee: Alcatel Lucent, Paris (FR)

( * ) Notice: Subject to any disclaimer, the term of this patent is extended or adjusted under 35 U.S.C. 154(b) by 0 days.

(21) Appl. No.: 13/284,868

(22) Filed: Oct. 28, 2011

(65) Prior Publication Data

US 2012/0107176 A1 May 3, 2012

Related U.S. Application Data

(60) Continuation of application No. 13/252,169, filed on Oct. 3, 2011, which is a continuation of application No. 13/020,446, filed on Feb. 3, 2011, now Pat. No. 8,066,945, which is a continuation of application No. 12/004,628, filed on Dec. 22, 2007, now abandoned, which is a division of application No. 11/119,519, filed on Apr. 30, 2005, now Pat. No. 7,341,692.

(51) Int. Cl.
*G01N 15/06* (2006.01)
*G01N 33/00* (2006.01)
*G01N 33/48* (2006.01)

(52) U.S. Cl.
USPC ........... 422/82.01; 422/50; 422/68.1; 422/81; 436/43; 436/63

(58) Field of Classification Search .............. 422/50, 422/68.1, 81, 82.01; 436/43, 63
See application file for complete search history.

(56) References Cited

U.S. PATENT DOCUMENTS

| 5,466,348 | A | 11/1995 | Holm-Kennedy |
| 6,109,094 | A | 8/2000 | Baranzahi |
| 6,150,604 | A | 11/2000 | Freundlich |
| 6,692,568 | B2 | 2/2004 | Cuomo |
| 6,763,699 | B1 | 7/2004 | Hunter |
| 7,151,301 | B2 | 12/2006 | Yoo |
| 7,179,639 | B2 * | 2/2007 | Pottathil et al. ............ 435/287.2 |
| 7,235,389 | B2 | 6/2007 | Lim |

(Continued)

OTHER PUBLICATIONS

Duan et al., "Synthesis and optical properties of gallium arsenide nanowires", (Feb. 2000), Applied Physics Letters, vol. 76, No. 9, pp. 1116-1118.

(Continued)

*Primary Examiner* — Brian J Sines
(74) *Attorney, Agent, or Firm* — Jay Brown Law Firm

(57) ABSTRACT

Apparatus comprising surface site comprising substantially inorganic surface having chemical composition selected from group consisting of metals, semiconductors, insulators, and mixtures thereof, the surface positioned within polypeptide bonding region and having selective bonding affinity for polypeptide; plurality of interlayers between which surface site is interposed; distal site end on surface site and distanced from interlayers, the surface being provided on distal site end; surface site and interlayers being interposed between first and second supports; first and second conductors provided on first and second supports and having respective first and second distal conductor ends positioned within polypeptide bonding region; conductors being capable of applying external voltage potential across polypeptide bonding region. Apparatus, optionally comprising such first and second supports and conductors; and comprising third conductor in electrical communication with surface site, the third conductor positioned for electrical communication with source of an external bias voltage. Techniques for making apparatus.

12 Claims, 14 Drawing Sheets

U.S. PATENT DOCUMENTS

| | | | |
|---|---|---|---|
| 7,282,329 | B2 | 10/2007 | Manalis |
| 7,291,496 | B2 | 11/2007 | Holm-Kennedy |
| 7,317,216 | B2 | 1/2008 | Holm-Kennedy |
| 7,329,387 | B2 | 2/2008 | Fukutani |
| 7,341,692 | B2 | 3/2008 | Willett |
| 7,361,946 | B2 | 4/2008 | Johnson |
| 7,385,266 | B2 | 6/2008 | Segal |
| 7,538,400 | B2 | 5/2009 | Segal |
| 7,659,149 | B2 | 2/2010 | Yoo |
| 7,686,929 | B2 | 3/2010 | Toumazou |
| 7,692,219 | B1 | 4/2010 | Holm-Kennedy |
| 8,066,945 | B2 | 11/2011 | Willett |
| 2003/0059955 | A1 | 3/2003 | Bamdad |
| 2003/0068900 | A1 | 4/2003 | Belcher |
| 2003/0215865 | A1 | 11/2003 | Mayer |
| 2006/0237310 | A1* | 10/2006 | Patel et al. ............... 204/400 |
| 2006/0263255 | A1* | 11/2006 | Han et al. ............... 422/83 |
| 2012/0088308 | A1 | 4/2012 | Willett |

OTHER PUBLICATIONS

Brown, "Metal-recognition by repeating polypeptides", Nature Biotechnology, (1997), vol. 15, pp. 269-272 (Abstract).

Wagner et al., "Bioreactive Self-Assembled Monolayers on Hydrogen-Passivated Si(111) as a New Class of Atomically Flat Substrates for Biological Scanning Probe...Microscopy", Journal of Structural Biology (1997), vol. 119, pp. 189-201.

Rezania et al., "Bioactivation of metal oxide surfaces. 1. Surface characterization and cell response," (Sep. 1999), Langmuir, vol. 15, No. 20, pp. 6931-6939 (Abstract).

Zhang et al., "Biological surface engineering: a simple system for cell pattern formation," (1999), Biomaterials, vol. 20, pp. 1213-1220.

Whaley et al., "Selection of peptides with semiconductor binding specificity for directed nanocrystal assembly," (Jun. 2000), Nature, vol. 405, pp. 665-668.

Veiseh et al., "Highly selective protein patterning on gold-silicon substrates for biosensor applications", (Aug. 2002), Langmuir, vol. 18, No. 17, pp. 6671-6678 (Abstract).

Aizenberg et al., "Factors Involved in the Formation of Amorphous and Crystalline Calcium Carbonate: A Study of an Ascidian Skeleton," (2002) J.Am.Chem.Soc. vol. 124, No. 1, pp. 32-39.

Gleason et al., "Patterning proteins and cells using two-dimensional arrays of colloids," (Feb. 2003), Langmuir, vol. 19, No. 3, pp. 513-518, (Abstract).

Mao et al., "Viral assembly of oriented quantum dot nanowires", (Jun. 2003) PNAS, vol. 100, No. 12, pp. 6946-6951.

Yea et al., "Dynamic Interfaces between Cells and Surfaces: Electroactive Substrates that Sequentially Release and Attach Cells," (2003), J.Am.Chem.Soc., vol. 125, pp. 14994-14995.

* cited by examiner

FIG. 3

SOLVENT=HEPES

| | Lys | Arg | His | Asp | Glu | Thr | Ser | Asn | Gln | Tyr | Pro | Met | Cys | Trp | Gly | Ala | Val | Ile | Leu | Phe |
|---|---|---|---|---|---|---|---|---|---|---|---|---|---|---|---|---|---|---|---|---|
| GaAs | 2.8 | 1.2 | 2.3 | 2.1 | 3.0 | 3.0 | 1.6 | 0.9 | 0.7 | <.5 | <.5 | 1.6 | 0.7 | <.5 | 2.1 | <.5 | 0.7 | <.5 | <.5 | <.5 |
| Si₃N₄ | 21 | 13 | 18 | 8.0 | 17 | 1.3 | 2.1 | 1.6 | 1.8 | 2.1 | 5.3 | 4.4 | 4.4 | 5.3 | 3.5 | 0.7 | <.5 | <.5 | <.5 | 0.7 |
| SiO₂ | 22 | 10 | 18 | 5.3 | 25 | 1.2 | 0.7 | 2.3 | 1.2 | 2.1 | 3.9 | 0.9 | 4.1 | 3.5 | 3.0 | <.5 | 0.7 | <.5 | <.5 | <.5 |
| AlGaAs | 4.8 | 4.4 | 3.5 | 13 | 8.5 | 4.1 | 3.5 | 5.4 | 4.4 | 2.1 | <.5 | 2.5 | 1.4 | <.5 | 3.5 | 3.5 | 3.2 | 3.7 | 1.2 | 1.4 |
| Al | 6.4 | 5.5 | 3.2 | 5.1 | 5.2 | 4.1 | 2.1 | 5.1 | 7.3 | 1.8 | 1.5 | 4.2 | 0.7 | 2.1 | 4.6 | 0.7 | 2.3 | 2.1 | 0.7 | 1.2 |
| Pt | 1.4 | 1.8 | 1.3 | 1.4 | 1.5 | <.5 | 0.7 | 1.3 | <.5 | <.5 | <.5 | 0.8 | 0.7 | <.5 | 0.6 | <.5 | <.5 | <.5 | <.5 | <.5 |
| Ti | 1.2 | 2.3 | 1.3 | 1.4 | 0.9 | 0.7 | 1.3 | 1.4 | <.5 | <.5 | 0.6 | 0.7 | <.5 | <.5 | 0.7 | <.5 | <.5 | <.5 | <.5 | <.5 |
| Au | 0.9 | <.5 | <.5 | 0.7 | 0.7 | <.5 | <.5 | 1.2 | <.5 | <.5 | <.5 | 0.7 | <.5 | <.5 | <.5 | <.5 | <.5 | <.5 | <.5 | <.5 |
| Pd | 1.3 | 1.4 | 1.2 | 0.7 | 0.7 | <.5 | 1.4 | 0.8 | 0.7 | 0.7 | 0.7 | 0.7 | 0.7 | 0.7 | 1.4 | <.5 | <.5 | <.5 | <.5 | <.5 |

POLAR-CHARGED | POLAR-NONCHARGED | NON-POLAR

FIG. 4

SOLVENT=DMSO

| | Lys | Arg | His | Asp | Glu | Thr | Ser | Asn | Gln | Tyr | Pro | Met | Cys | Trp | Gly | Ala | Val | Ile | Leu | Phe |
|---|---|---|---|---|---|---|---|---|---|---|---|---|---|---|---|---|---|---|---|---|
| GaAs | <.5 | <.5 | <.5 | 1.6 | 2.1 | <.5 | <.5 | <.5 | <.5 | <.5 | <.5 | 0.7 | 0.7 | <.5 | <.5 | <.5 | <.5 | <.5 | <.5 | <.5 |
| Si$_3$N$_4$ | 18 | 21 | 18 | 6.8 | 12 | 2.1 | 0.7 | 1.2 | <.5 | 2.1 | 1.4 | 3.5 | 3.7 | 2.5 | 3.5 | <.5 | 1.2 | 3.5 | <.5 | 1.8 |
| SiO$_2$ | 11 | 15 | 20 | 5.6 | 17 | 2.1 | 1.2 | 1.6 | <.5 | 1.4 | <.5 | 4.6 | 3.4 | 4.4 | 3.5 | 2.1 | 1.4 | 2.3 | <.5 | 0.9 |
| AlGaAs | 1.8 | <.5 | 0.9 | 3.7 | 10 | 5.5 | 1.4 | 2.1 | <.5 | <.5 | <.5 | 1.2 | <.5 | <.5 | 1.4 | 1.4 | 1.6 | <.5 | <.5 | 2.5 |
| Al | 0.7 | <.5 | <.5 | 4.6 | 3.7 | 4.4 | 0.7 | 0.7 | 0.6 | 1.2 | 0.7 | 1.6 | 0.7 | 0.7 | 1.4 | 0.7 | 3.5 | 0.7 | <.5 | 0.6 |
| Pt | 1.3 | <.5 | <.5 | 1.4 | 0.7 | <.5 | 0.7 | <.5 | 0.6 | <.5 | <.5 | 1.4 | <.5 | <.5 | <.5 | <.5 | <.5 | <.5 | <.5 | <.5 |
| Ti | <.5 | <.5 | <.5 | 1.3 | 0.9 | <.5 | 0.6 | <.5 | 0.7 | <.5 | <.5 | <.5 | <.5 | <.5 | <.5 | <.5 | <.5 | <.5 | <.5 | <.5 |
| Au | <.5 | <.5 | <.5 | 0.7 | <.5 | <.5 | 2.3 | <.5 | <.5 | 0.6 | <.5 | 0.9 | <.5 | <.5 | <.5 | <.5 | <.5 | <.5 | <.5 | <.5 |
| Pd | 1.2 | <.5 | <.5 | 0.7 | <.5 | <.5 | <.5 | <.5 | <.5 | 0.7 | <.5 | <.5 | <.5 | <.5 | <.5 | <.5 | <.5 | <.5 | <.5 | <.5 |

POLAR-CHARGED: Lys, Arg, His, Asp, Glu
POLAR-NONCHARGED: Thr, Ser, Asn, Gln, Tyr, Pro
NON-POLAR: Met, Cys, Trp, Gly, Ala, Val, Ile, Leu, Phe

FIG. 16

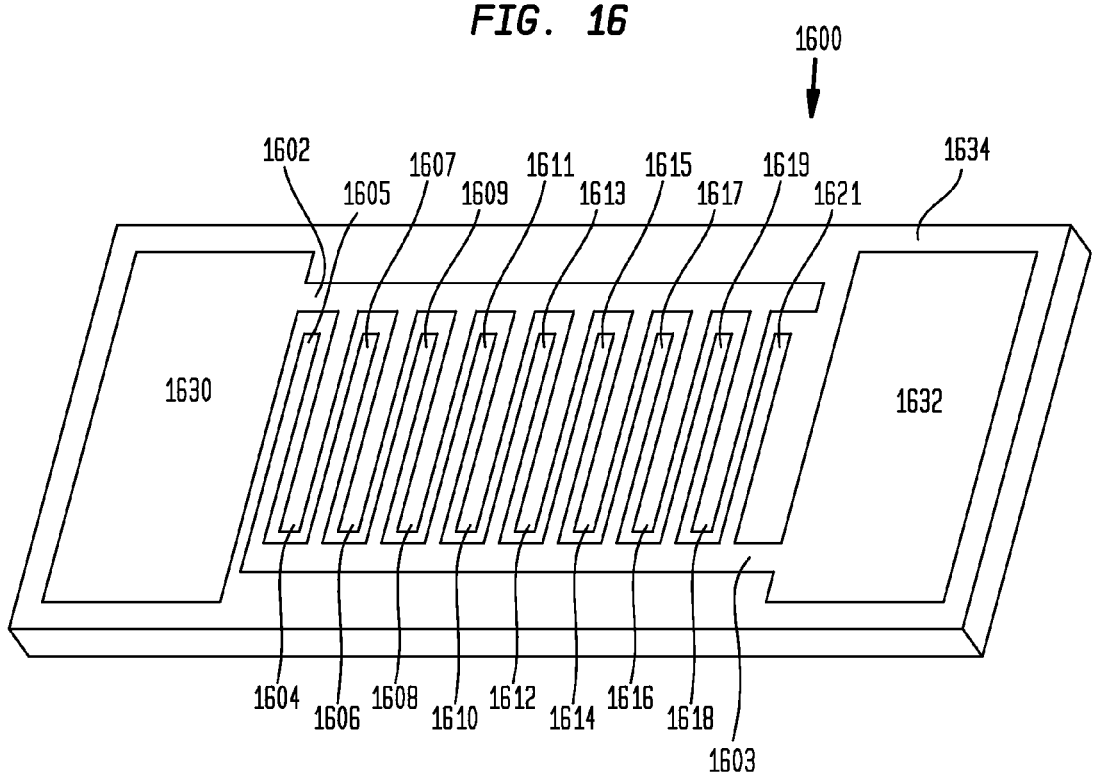

FIG. 17

METHOD OF MAKING AMINO ACID DETECTION AND IDENTIFICATION APPARATUS

- 1705: PROVIDE SUBSTRATE FOR TEST CELLS, HAVING AN OUTER BOUNDARY WALL, AND BOUNDARY WALLS SEPARATING THE TEST CELLS
- 1710: PROVIDE BOTTOM SURFACES IN TEST CELLS, COMPRISING A SELECTED SUBSTANTIALLY INORGANIC METAL, SEMICONDUCTOR, AND/OR INSULATOR HAVING SELECTIVE AMINO ACID AFFINITY
- 100: AMINO ACID DETECTION AND IDENTIFICATION APPARATUS

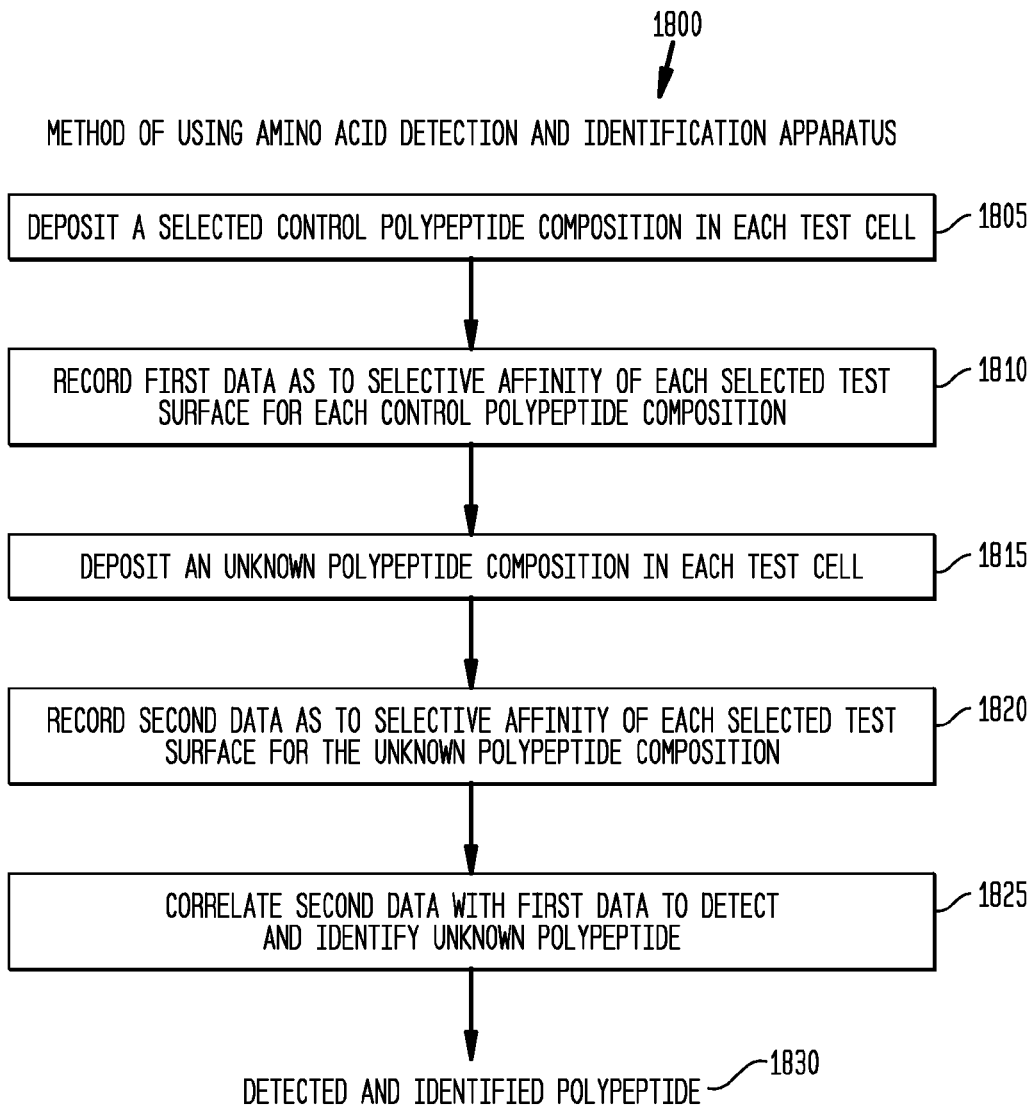

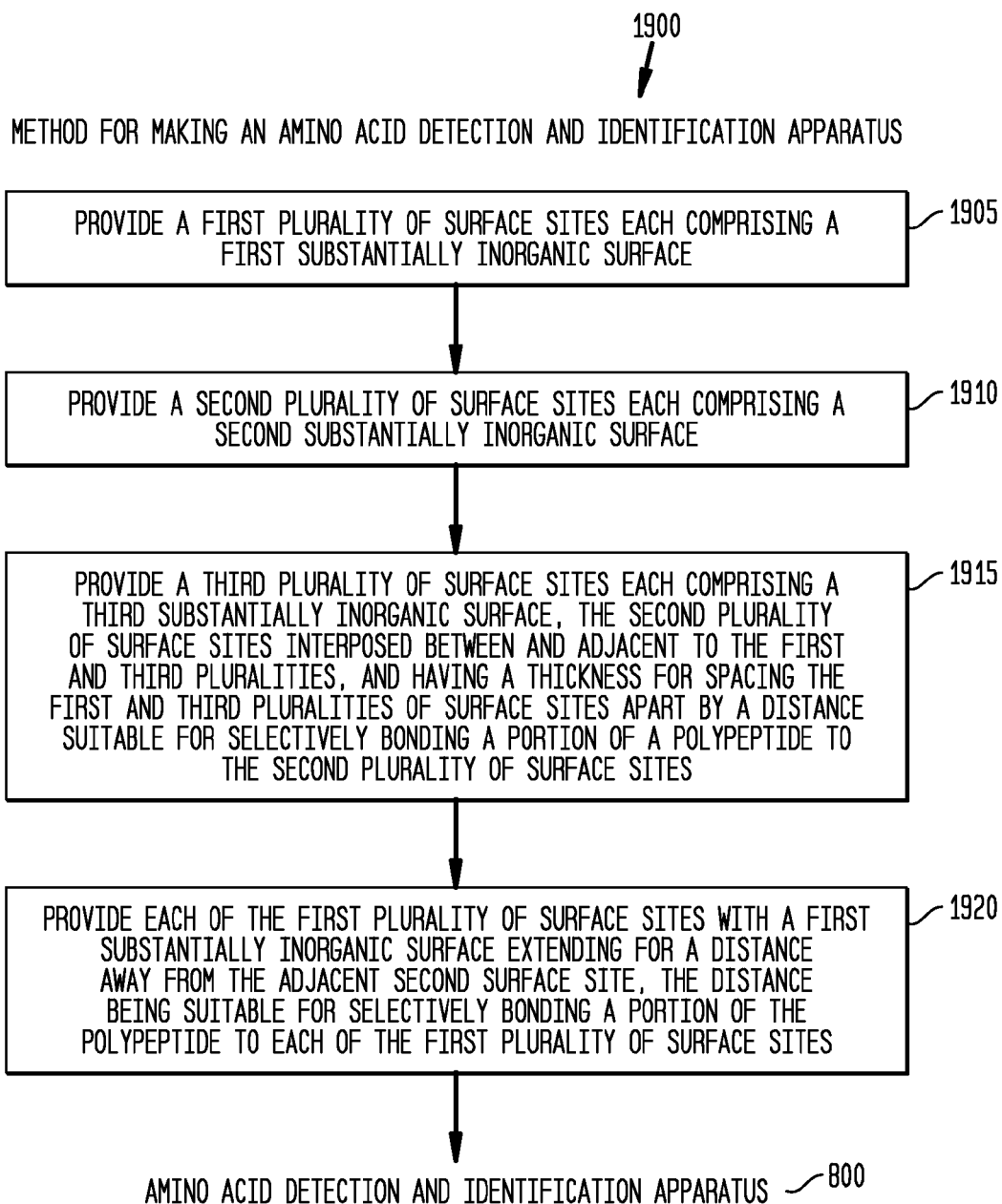

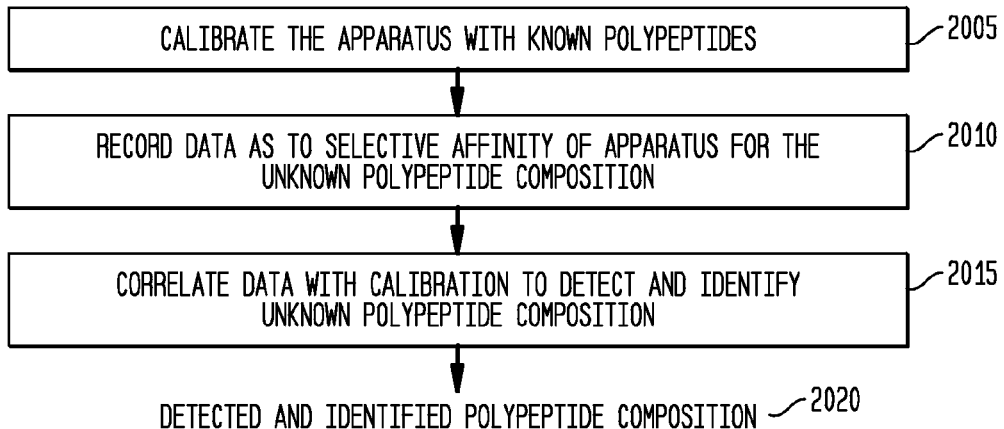
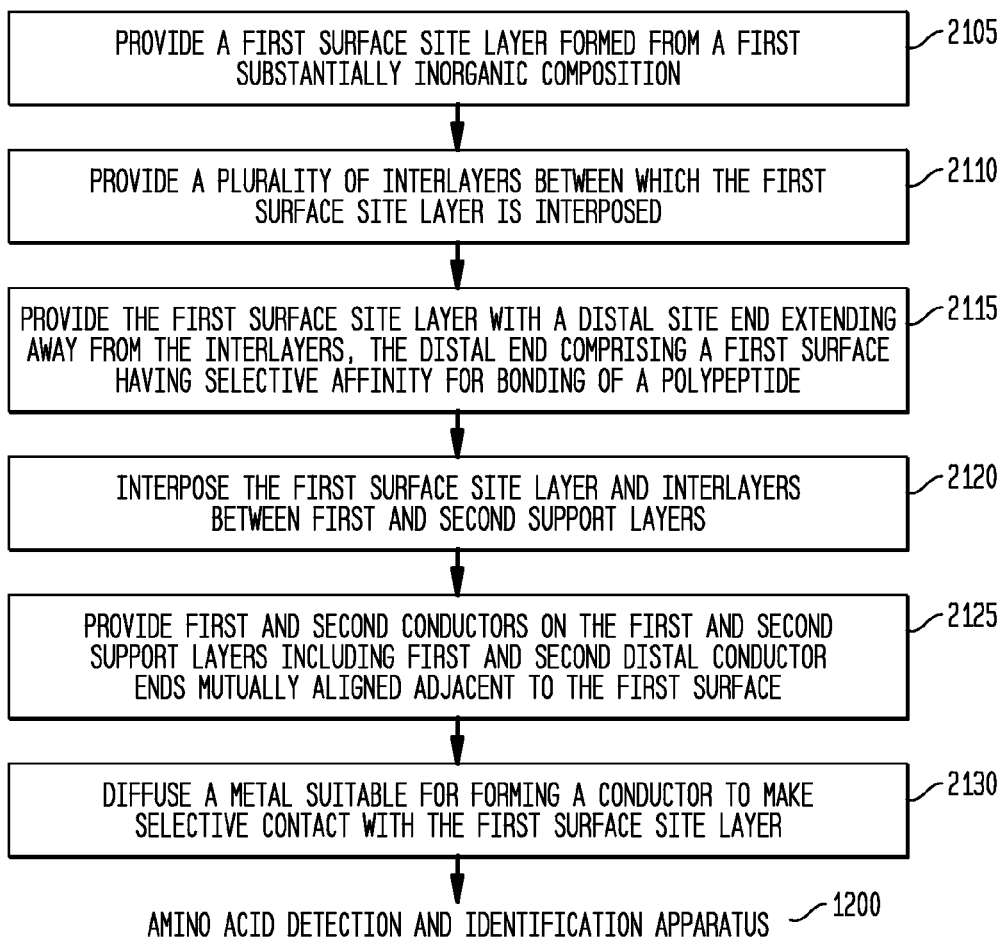

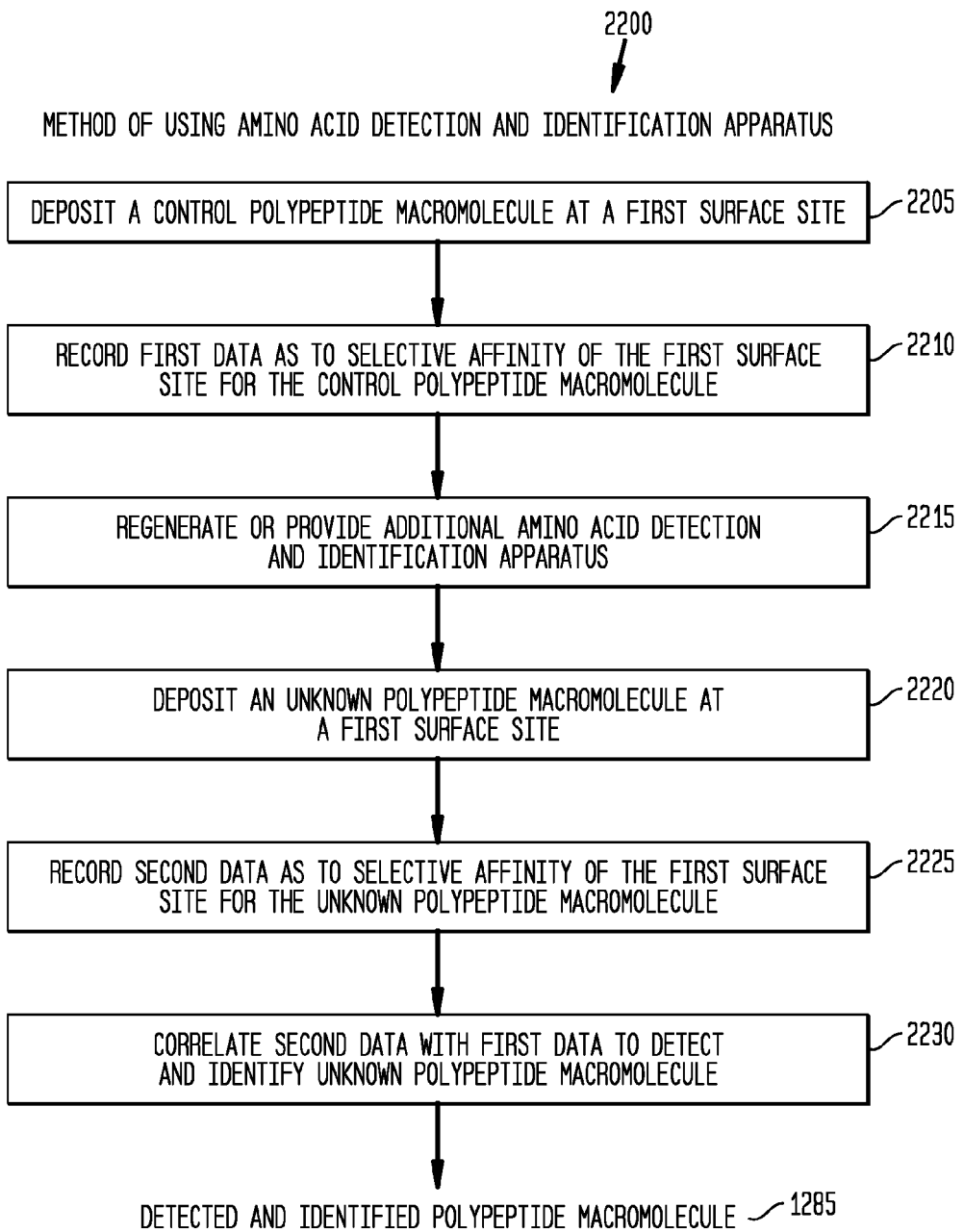

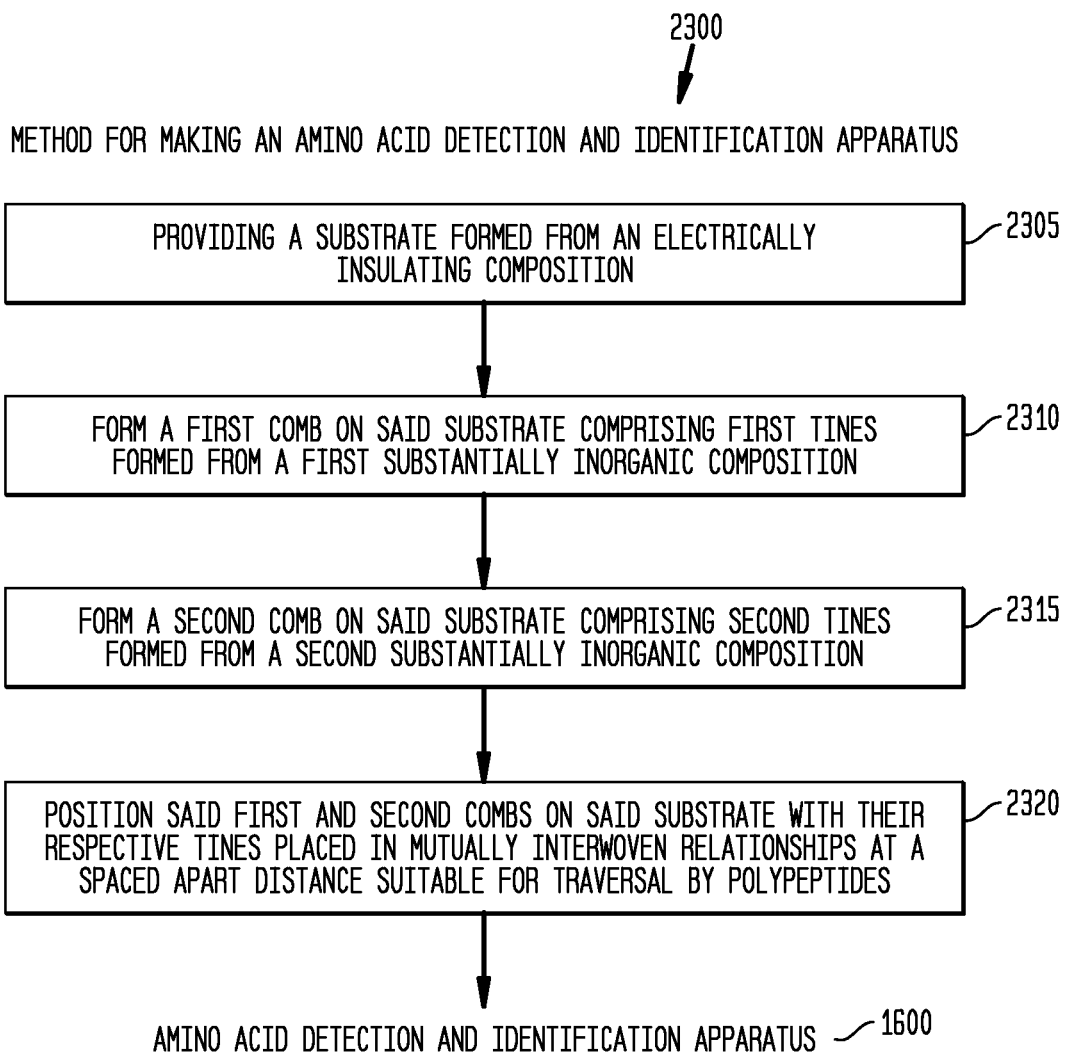

DETECTION APPARATUS FOR BIOLOGICAL MATERIALS AND METHODS OF MAKING AND USING THE SAME

FIELD OF THE INVENTION

This invention relates to the field of apparatus for the detection, identification, characterization and further analysis of biological materials.

BACKGROUND OF THE INVENTION

Tremendous progress has been made over several decades in the study of biological materials ranging from amino acids, to proteins, to the entire human genome. In spite of the great strides that have already been made, cost-effective and timely analysis of biological materials frequently is still not a reality. For the myocardial infarction victim waiting in the hospital emergency room or undergoing a heart bypass operation, the time needed for conventional blood analysis in order to detect the telltale enzyme signature of a heart attack may be too long. Myriad other circumstances can be observed in which analytical test results on biological materials simply take too long to generate, aren't available where needed, and cost too much. Furthermore, conventional diagnostic tests typically are encumbered by their own particular collection of analytical inadequacies, leading to false positive and negative results at levels that are both intractable and statistically significant.

Accordingly, there is a continuing need for analytical apparatus that can be used to detect, identify, characterize and otherwise analyze biological materials, including for example amino acids and proteins.

SUMMARY OF THE INVENTION

Apparatus are provided comprising substantially inorganic surfaces comprising metals, semiconductors and/or insulators, which selectively bond amino acids, polypeptides, proteins, and/or other substances comprising amino acids. The selective bonding enables the detection, identification, and/or further analysis of the target amino acid-comprising materials.

In one embodiment, an apparatus is provided, comprising: a first surface site comprising a first substantially inorganic surface having a first chemical composition selected from the group consisting of metals, semiconductors, insulators, and mixtures thereof, said first surface positioned within a polypeptide bonding region and having a selective bonding affinity for a polypeptide; a plurality of first interlayers between which said first surface site is interposed; a first distal site end on said first surface site and distanced from said first interlayers, said first surface being provided on said first distal site end; said first surface site and said first interlayers being interposed between first and second supports; first and second conductors provided on said first and second supports and having respective first and second distal conductor ends positioned within said polypeptide bonding region; said conductors being capable of applying an external voltage potential across said polypeptide bonding region.

In another embodiment, an apparatus is provided, comprising: a first surface site comprising a first substantially inorganic surface having a first chemical composition selected from the group consisting of metals, semiconductors, insulators, and mixtures thereof, said first surface positioned within a polypeptide bonding region and having a selective bonding affinity for a polypeptide; a plurality of first interlayers between which said first surface site is interposed; a first distal site end on said first surface site and distanced from said first interlayers, said first surface being provided on said first distal site end; and a first conductor in electrical communication with said first surface site, said first conductor positioned for electrical communication with a source of an external bias voltage.

In a further embodiment, a method of making an apparatus is provided, comprising the steps of: providing a first surface site comprising a first substantially inorganic surface having a first chemical composition selected from the group consisting of metals, semiconductors, insulators, and mixtures thereof, having a selective bonding affinity for a polypeptide; positioning said first surface within a polypeptide bonding region; interposing said first surface site between a plurality of first interlayers; providing a first distal site end on said first surface site and distancing said first distal site end from said first interlayers; providing said first surface on said first distal site end; interposing said first surface site and said first interlayers between first and second supports; and providing first and second conductors on said first and second supports, having respective first and second distal conductor ends positioned within said polypeptide bonding region.

BRIEF DESCRIPTION OF THE DRAWINGS

FIG. 3 shows another array of exemplary control test data for polypeptides, generated using the amino acid detection and identification apparatus of FIG. 1;

FIG. 4 shows a further array of exemplary control test data for polypeptides, generated using the amino acid detection and identification apparatus of FIG. 1;

FIG. 16 shows a perspective view of an embodiment of an additional amino acid detection and identification apparatus;

FIG. 17 shows steps of a method for making the amino acid detection and identification apparatus of FIG. 1;

FIG. 18 shows steps of a method for using the apparatus of FIG. 1 for detection and identification of an unknown polypeptide in a fluid;

FIG. 19 shows steps of a method for making the amino acid detection and identification apparatus shown in FIGS. 8 and 9;

FIG. 20 shows steps of a method for using the apparatus of FIGS. 8 and 9 for detection and identification of an unknown polypeptide in a fluid;

FIG. 21 shows steps of a method for making the amino acid detection and identification apparatus shown in FIGS. 12, 13 and 14;

FIG. 22 shows steps of a method for using the apparatus of FIGS. 12, 13 and 14 for detection and identification of an unknown polypeptide macromolecule in a fluid; and FIG. 23 shows steps of a method for making the amino acid detection and identification apparatus shown in FIG. 16.

DETAILED DESCRIPTION

Apparatus are provided for the detection, identification, characterization, and other analysis of biological materials. The biological materials to be analyzed can include, for example, amino acids, polypeptides, and proteins. The detection apparatus comprise defined surfaces constituted by substantially inorganic materials including metals, semiconductors, and/or insulators, to which biological materials selectively adhere in differential manners depending on the natures of the particular surfaces and biological materials. Following adhesion of biological materials to the apparatus, such materials can be optically and electronically and otherwise analyzed in order to detect, identify and characterize the materials. By "substantially inorganic" herein is meant that the predominant components of the surface compositions do not comprise organic materials. However, it is to be understood that the incorporation of minor concentrations of organic materials that do not materially detract from the selective bonding affinity of the substantially inorganic materials employed, is within the scope of these teachings. By "organic" is meant a composition comprising a carbon chain.

Figure 1:
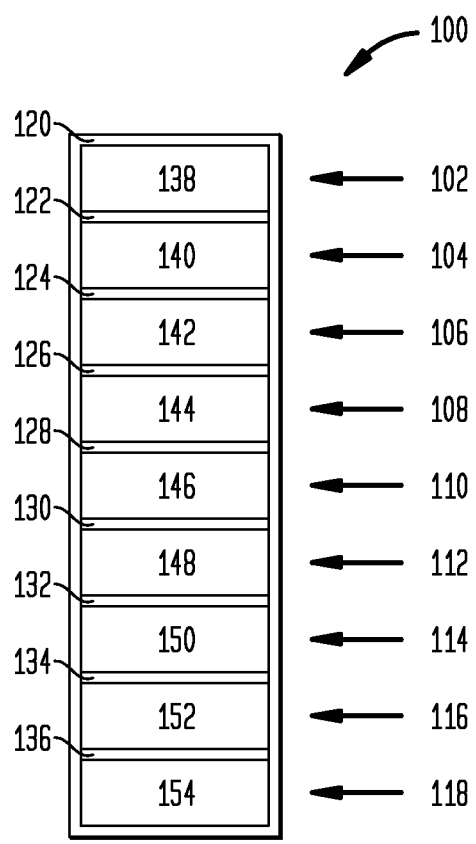
FIG. 1 shows a top view of an embodiment of an amino acid detection and identification apparatus.

FIG. 1 shows a top view of an embodiment of an amino acid detection and identification apparatus 100. The apparatus 100 is constituted by a column of test cells 102, 104, 106, 108, 110, 112, 114, 116 and 118. In one embodiment, the test cells 102-118 are made from polished undoped GaAs wafers having a [100] orientation. The test cells 102-118 are collectively capable of containing a sample of an amino acid or polypeptide solution within a raised outer boundary wall 120, and if desired can be mutually separated by boundary walls 122, 124, 126, 128, 130, 132, 134 and 136. The cells 102-118 have bottom surfaces 138, 140, 142, 144, 146, 148, 150, 152 and 154 respectively, each comprising a selected inorganic metal, semiconductor, and/or insulator surface that selectively adheres amino acids and polypeptides. In this embodiment, the metals palladium (Pd), gold (Au), titanium (Ti), platinum (Pt), and aluminum (Al); the semiconductors gallium-arsenide (GaAs), and aluminum-gallium-arsenide (AlGaAs); and the insulators silicon nitride ($Si_3N_4$), and silicon dioxide ($SiO_2$), were used. Accordingly, the bottom surfaces 138, 140, 142, 144, 146, 148, 150, 152 and 154 respectively comprise: GaAs, $Si_3N_4$, $SiO_2$, AlGaAs, Al, Pt, Ti, Au, and Pd. In one embodiment, the AlGaAs was $Al_xGa_{(1-x)}As$ with x=about 0.3.

In one embodiment, optical characteristics of each of the bottom surfaces 138, 140, 142, 144, 146, 148, 150, 152 and 154 are recorded as control data in the absence of a test solution. For example, the optical characteristics can be determined using equipment suitable for detecting and recording the optical absorption and reflectance of each of the bottom surfaces 138, 140, 142, 144, 146, 148, 150, 152 and 154. In this regard, the apparatus 100 desirably includes test cells 102, 104, 106, 108, 110, 112, 114, 116 and 118 arranged in a regular array. The test cells are carefully aligned for reading by corresponding equipment suitable for detecting and recording the optical absorption and reflectance of each of the bottom surfaces 138, 140, 142, 144, 146, 148, 150, 152 and 154. It is understood that the vertical alignment of the test cells 102, 104, 106, 108, 110, 112, 114, 116 and 118 in a column is merely exemplary. For example, analogous test cell arrays can comprise horizontal rows as well as multiple rows and columns, or other regular arrays such as test cells arranged in concentric circles. Test cells can also be individually configured and analyzed.

A test solution comprising an unknown amino acid or polypeptide is applied to the respective bottom surfaces 138, 140, 142, 144, 146, 148, 150, 152 and 154 of the test cells 102, 104, 106, 108, 110, 112, 114, 116 and 118. After allowing the passage of a suitable time period for any bonding of the test solution components on the bottom surfaces to occur, such as about three (3) hours, the test solution is removed from the test cells 102-118 and the test cells are rinsed several times using a test solution solvent. If present in the test solution, an unknown amino acid or polypeptide will selectively bond to some or all of the bottom surfaces 138, 140, 142, 144, 146, 148, 150, 152 and 154. The optical characteristics of the apparatus 100 are then determined, using the same equipment for detecting and recording the optical absorption and reflectance of each of the bottom surfaces. Changes in such absorption and reflectance on some or all of the bottom surfaces 138, 140, 142, 144, 146, 148, 150, 152 and 154 are then computed by comparison with the corresponding control data. Such changes in optical absorption and reflectance on the bottom surfaces 138, 140, 142, 144, 146, 148, 150, 152 and 154 collectively constitute a signature for identification of a particular amino acid or polypeptide present in the test solution. For example, known samples of monomers or polypeptides of each of the twenty amino acids lysine (Lys), arginine (Arg), histidine (His), aspartic acid (Asp), glutamic acid (Glu), threonine (Thr), serine (Ser), asparagine (Asn), glutamine (Gln), tyrosine (Tyr), proline (Pro), methionine (Met), cysteine (Cys), tryptophan (Trp), glycine (Gly), alanine (Ala), valine (Val), isoleucine (Ile), leucine (Leu), and phenylalanine (Phe) can separately be subjected to these same steps. Such known polypeptides are commercially available, for example, from Anaspec Inc., San Jose, Calif. These polypeptides can be made by solid state synthesis. Background information is provided in Merryfield, R. B., *J. Am. Chem. Soc.*, Vol. 85, pp. 2149+ (1963), the entirety of which hereby is incorporated herein by reference. The resulting data can be recorded as unique signatures for each such amino acid or polypeptide. A test solution comprising a given unknown amino acid or polypeptide can then be identified by comparing the control signature data to test data computed on the unknowns using the apparatus 100. In another embodiment, all of the amino acid or polypeptide solutions can be tagged, such as by fluorescence, radioactivity, or ligands having known bonding activity. In the latter case, for example, bonding pairs such as biotin-avidin or antigen-antibody can be employed. The cells are then developed, such as by the measurement of fluorescence, radioactivity, or bonding affinity with marked bonding pair counterparts, and the relative and absolute strength of bonding in each test cell is read.

In one embodiment, the following test solution application procedure was used. An apparatus 100 having a bottom surface with dimensions of about 2 millimeters by 2 millimeters patterned on a GaAs substrate was placed in the respective test solution and left for about 3 hours. The apparatus 100 was then removed from the test solution and rinsed in deionized water for 10 seconds and then dried in nitrogen gas.

There are four different classes of amino acids as determined by their side chains, including polar-acidic, polar-basic, polar-neutral, and non-polar neutral amino acids. The polar-acidic amino acids include Asp and Glu. The polar-basic amino acids include Lys, Arg and His. The polar-neutral amino acids include Thr, Ser, Asn, Gln, Tyr and Pro. The non-polar neutral amino acids include Met, Cys, Trp, Gly, Ala, Val, Ile, Leu and Phe. Desirably, each of these four groups of amino acids is considered to have bonding behavior on the bottom surfaces 138, 140, 142, 144, 146, 148, 150, 152 and 154 that is somewhat consistent within the group. This consistency can aid in identification of test solutions containing unknown amino acids and polypeptides. In general, the polar amino acids, including the polar-acidic, polar-basic, and polar-neutral amino acids, are hydrophilic and accordingly may be soluble in polar solvents which are used in the test solutions. For example, water can be used as the solvent. In general, the non-polar neutral amino acids are hydrophobic and accordingly may be soluble in nonpolar solvents such as nonpolar hydrocarbons. Polar amino acids may also be somewhat soluble in nonpolar solvents, and nonpolar amino acids may also be somewhat soluble in polar solvents.

The amino acid detection and identification apparatus 100 is particularly suitable for the testing and identification of individual amino acids and polypeptides of individual amino acids. In general, solutions containing more than one amino acid are desirably separated using conventional techniques before amino acid identification using the amino acid detection and identification apparatus 100. Separation can be carried out, for example, using a chromatography column or electrophoresis gel.

Figure 2:
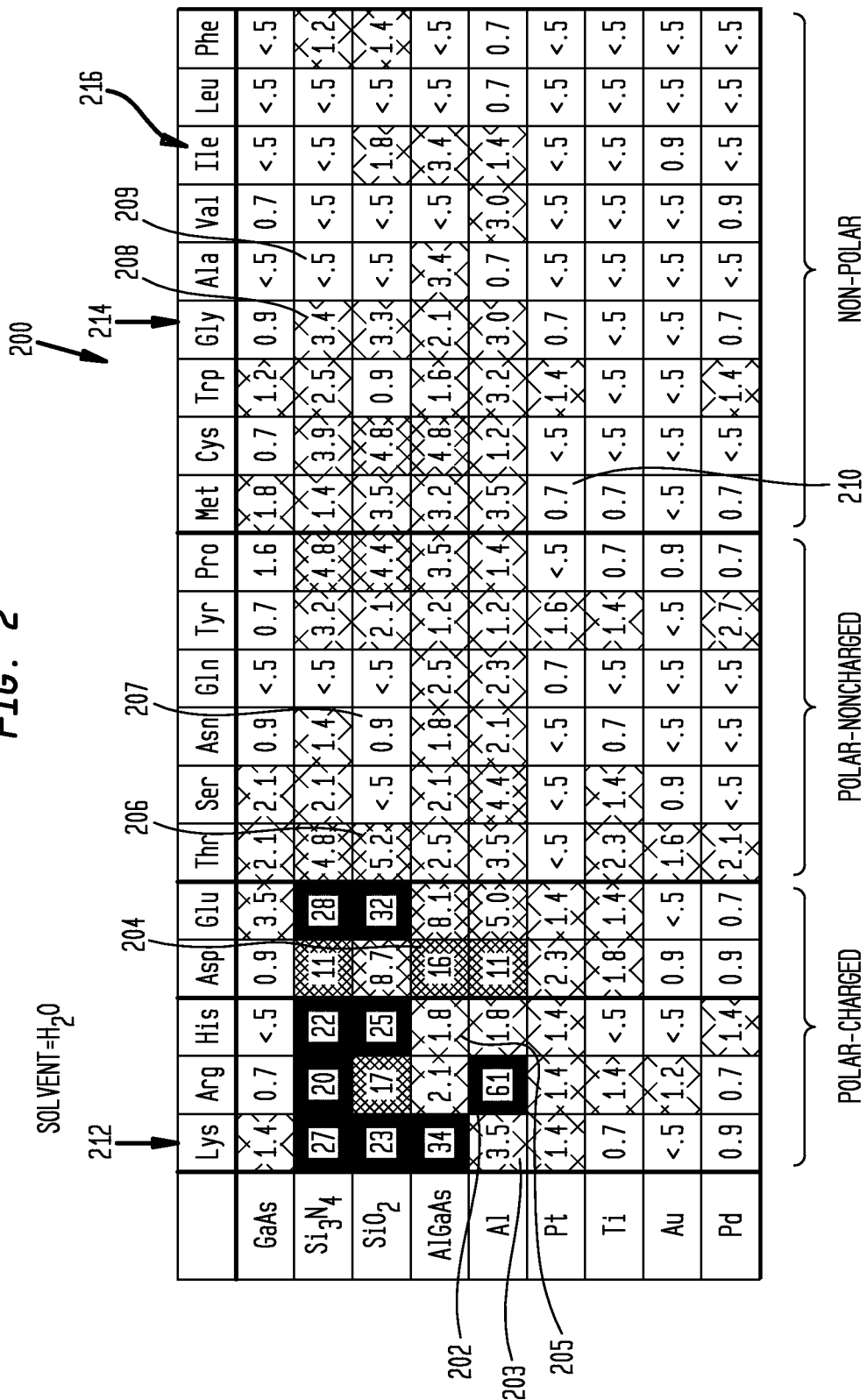
FIG. 2 shows an array of exemplary control test data for polypeptides, generated using the amino acid detection and identification apparatus of FIG. 1.

FIG. 2 shows an array 200 of exemplary control test data for polypeptides of each of the 20 amino acids, generated using the amino acid detection and identification apparatus 100. The polypeptides were separately prepared for each amino acid, generally having chain lengths of ten (10) amino acid moieties except for minor concentrations of peptides having chain lengths of eight (8) amino acid moieties. Other species may be present at insubstantial concentrations. Each polypeptide further included a 5-carboxyfluorescein (5F-AM) moiety bound at the exposed —N—H$_2$ group at the polypeptide end, leaving an exposed —C—O—O—H (carboxylic acid) group at the other end. Although the exposed —C—O—O—H groups are themselves reactive, this reactivity is overshadowed by the comparatively greater cumulative reactivity of the various side chains also present in each amino acid moiety, of which there accordingly are generally eight (8) or ten (10) in each polypeptide. Therefore, bonding of the polypeptides to the substantially inorganic bottom surfaces occurs through these side chains, a longitudinal side of the polypeptide thus being secured to the bottom surface. Although some end-bonding of polypeptides through the exposed —C—O—O—H groups may transiently occur, such bonding is disfavored due to entropy and other factors, and unlikely to persist. Since each polypeptide comprises such an exposed —C—O—O—H group, strong bonding there would lead to indistinguishable results among testing of various polypeptides. Hence, operation of the amino acid detection and identification apparatus 100 takes advantage of the dynamics of this bonding environment to provide test results facilitating differentiation between polypeptides of different amino acids. In alternative embodiments, fluorescein, or fluorescein 5-isothiocyanate (FITC), are used as markers instead of 5F-AM. In the case of Cys polypeptides, the following peptide sequence was used in view of the potential for excessive disulfide crosslinking: 5F-AM-Ala-Cys-Ala-Ala-Ala-Cys-Ala-Ala-Ala-OH. A potential source of variability in the results is the presence of contaminants in the polypeptides that could induce or block adhesion to the substantially inorganic surfaces.

In this exemplary embodiment, each of the 20 polypeptides was separately dissolved in water to generate the control solutions for testing. In one embodiment, a 1.0 millimolar concentration of the polypeptides was used. The left-most column of FIG. 2 shows row headings for the control test data array. The row headings identify and correspond to the metals, semiconductors and insulators on the bottom surfaces 138, 140, 142, 144, 146, 148, 150, 152 and 154 respectively of the amino acid detection and identification apparatus 100. The top-most row of FIG. 2 shows column headings for the control test data array. The column headings identify and correspond to the individual known polypeptide solutions that were separately tested as reported in each column of the control test data array.

The control test data array shown in FIG. 2 is indicative of the relative and numerical concentrations of polypeptides bound to the indicated substantially inorganic surfaces when the test cells of the amino acid detection and identification apparatus 100 were subjected to known aqueous solutions of each individual polypeptide. The units of the numerical data are in $1 \times 10^3$ polypeptides per square micrometer ($\mu m^2$). The margin of error in the data was about twenty percent (20%). This margin of error included both statistical error and systematic error. Systematic errors include, for example, variations in results due to differences in the processes for preparation of and of the concentrations in the polypeptide solutions. The impact of margin of error effects on the reliability and repeatability of test results can be moderated by carrying out multiple trials and then averaging the numerical results.

The control test cell data for the polar-acidic and polar-basic polypeptides of Lys, Arg, His, Asp and Glu are grouped together in the left section of the test cell data array shown in FIG. 2. The test cell data for the polar-neutral polypeptides of Thr, Ser, Asn, Gln, Tyr and Pro are grouped together in the middle section of the test cell data array. The test cell data for the remaining non-polar neutral polypeptides of Met, Cys, Trp, Gly, Ala, Val, Ile, Leu and Phe are grouped together in the right section of the test cell data array. Each of the data in the test cell data array visually and numerically indicates the degree to which the designated polypeptide in each test bonded to the designated substantially inorganic surface. For example, data point 202 shows that an aqueous solution of polar-basic Arg polypeptide strongly bonded to Al, as indicated both by the dark shading and the high numerical reading, $61 \times 10^3/\mu m^2$. Data point 203 shows, in contrast, that the Lys polypeptide only lightly bonded to Al, as indicated both by the light shading and the light reading, $3.5 \times 10^3/\mu m^2$. Further for example, data point 204 shows that an aqueous solution of polar-acidic Asp polypeptide firmly bonded to AlGaAs, as indicated both by the medium dark shading and the elevated numerical reading, $16 \times 10^3/\mu m^2$. Data point 205 shows, in contrast, that the His polypeptide only lightly bonded to AlGaAs, as indicated both by the light shading and the light reading, $1.8 \times 10^3/\mu m^2$. Additionally for example, data point 206 shows that an aqueous solution of polar-neutral Thr polypeptide moderately bonded to $SiO_2$, as indicated both by the grey shading and the moderate numerical reading, $5.2\times10^3/\mu m^2$. Data point 207 shows, in contrast, that Asn polypeptide only minimally bonded to $SiO_2$, as indicated both by the lack of shading and the low numerical reading, $0.9\times10^3/\mu m^2$. Furthermore for example, data point 208 shows that an aqueous solution of non-polar neutral Gly polypeptide lightly bonded to $Si_3N_4$, as indicated both by the light shading and the light reading, $3.4\times10^3/\mu m^2$. Data point 209 shows, in contrast, that Ala polypeptide only minimally bonded to $Si_3N_4$, as indicated both by the lack of shading and the low numerical reading, less than (<) $0.5\times10^3/\mu m^2$. In addition, for example, data point 210 shows that an aqueous solution of non-polar neutral Met polypeptide minimally bonded to Pt, as indicated both by the lack of shading and the low numerical reading, $0.7\times10^3/\mu m^2$.

The visual and numerical test data reflected in the control test data array 200 can be used to identify the amino acid content of unknown aqueous polypeptide solutions. The control test data array in FIG. 2 shows the strength of the bonding that results from exposure of each of the nine substantially inorganic surfaces separately to each of the twenty amino acid oligomers (polypeptides). The strength of such bonding, ranging from strong, to firm, moderate, light, and minimal, constitutes an indication of the amino acid identity as correlated with the data in FIG. 2. FIG. 2 shows that most of the strongest bonding reactions occurred with polar-acidic and polar-basic polypeptides, and that the strongest bonding reactions involved the $Si_3N_4$, $SiO_2$, AlGaAs, and Al surfaces. However, each of the control tests reported in the array did generate a numerical bonding reading. In addition, each of the exemplary control tests reported in columns 212, 214 and 216 generated a different series of readings for the nine substantially inorganic test surfaces. For example, Gly polypeptide in column 214 lightly bonded to $Si_3N_4$, $SiO_2$ and AlGaAs, but Ile polypeptide in column 216 lightly bonded only to $SiO_2$ and AlGaAs, and instead minimally bonded to $Si_3N_4$. These different series of numerical polypeptide bonding values can be used as signatures to distinguish Gly from Ile. Further analogous series of numerical bonding values can be used to identify other polypeptides in a test solution that is applied to the apparatus 100. The numerical bonding values for a given polypeptide are generally independent of the concentration of the polypeptides in solution, provided that bonding surface saturation by polypeptides occurs. Where, as reported in FIG. 2, oligomers of individual amino acids are tested, the test data reflect the concentration of the polypeptides rather than of the individual amino acid molecules. The units are calibrated to $1\times10^3$ amino acid oligomers per square micrometer.

FIG. 3 shows another array 300 of exemplary control test data for oligomers of the 20 amino acids prepared in the same manner as described above in connection with FIG. 2, generated using the amino acid detection and identification apparatus 100. In this exemplary embodiment, each of the twenty amino acid oligomers so tested was constituted in a 0.25 molar polypeptide solution using 1 Molar (N-2-[hydroxyethyl]piperazine-N'-[2-ethanesulfonic acid]) (HEPES) diluted in water, in order to generate the control solutions for testing. As in FIG. 2, the left-most column of FIG. 3 shows row headings for the control test data array. The row headings identify and correspond to the metals, semiconductors and insulators on the bottom surfaces 138, 140, 142, 144, 146, 148, 150, 152 and 154 respectively of the amino acid detection and identification apparatus 100. The top-most row of FIG. 3 shows column headings for the control test data array. The column headings identify and correspond to the individual known polypeptide solutions that were separately tested as reported in each column of the control test data array. The numerical data are again reported in units of $1\times10^3$ amino acid oligomer molecules per square micrometer. The control test data array shown in FIG. 3 is indicative of the relative concentrations of polypeptides bound to the indicated substantially inorganic surfaces when the test cells of the amino acid detection and identification apparatus 100 were subjected to known HEPES solutions of each individual polypeptide.

Each of the data in the test cell data array 300 visually and numerically indicates the degree to which the designated polypeptide in each test bonded to the designated substantially inorganic surface. For example, data point 302 shows that a HEPES solution of polar-basic Lys polypeptide strongly bonded to $Si_3N_4$, as indicated both by the dark shading and the high numerical reading, $21\times10^3/\mu m^2$. Data point 303 shows, in contrast, that Ser polypeptide only lightly bonded to $Si_3N_4$, as indicated both by the light shading and the light reading, $2.1\times10^3/\mu m^2$. Further for example, data point 304 shows that a HEPES solution of polar-neutral Thr polypeptide firmly bonded to $SiO_2$, as indicated both by the medium dark shading and the elevated numerical reading, $12\times10^3/\mu m^2$. Data point 305 shows, in contrast, that Asn polypeptide only lightly bonded to $SiO_2$, as indicated both by the light shading and the light reading, $2.3\times10^3/\mu m^2$. Additionally for example, data point 306 shows that a HEPES solution of non-polar neutral Met polypeptide moderately bonded to $Si_3N_4$, as indicated both by the grey shading and the moderate numerical reading, $4.4\times10^3/\mu m^2$. Data point 307 shows, in contrast, that Gln polypeptide only lightly bonded to $Si_3N_4$, as indicated both by the light shading and the light reading, $1.8\times10^3/\mu m^2$. Furthermore for example, data point 308 shows that a HEPES solution of non-polar neutral Gly polypeptide lightly bonded to $SiO_2$, as indicated both by the light shading and the light reading, $3.0\times10^3/\mu m^2$. Data point 309 shows, in contrast, that Ala polypeptide only minimally bonded to $SiO_2$, as indicated both by the lack of shading and the low numerical reading, $<0.5\times10^3/\mu m^2$. In addition, for example, data point 310 shows that a HEPES solution of non-polar neutral Ala polypeptide minimally bonded to Al, as indicated both by the lack of shading and the low numerical reading, $0.7\times10^3/\mu m^2$. FIG. 3 shows the strength of the bonding that resulted from exposure of each of the nine substantially inorganic surfaces separately to each of the twenty amino acid oligomers. As in the case of FIG. 2, FIG. 3 shows that most of the strongest bonding reactions occurred with polar-acidic and polar-basic polypeptides, and that the strongest bonding reactions involved the $Si_3N_4$, $SiO_2$, AlGaAs, and Al surfaces. However, each of the test cells did generate a numerical data reading. In addition, each of the exemplary test data columns 312, 314, and 316 generated a different series of readings for the nine test surfaces. For example, Ile polypeptide in column 314 moderately bonded to Al and lightly bonded to $SiO_2$, but Leu polypeptide in column 316 only lightly bonded to Al, and minimally bonded to $SiO_2$. These differential bonding patterns can be used to distinguish Ile from Leu. Further differential bonding patterns potentially can be mapped from the FIG. 3 data and used to distinguish any two HEPES amino acid oligomer solutions from each other in a likewise manner.

FIG. 4 shows a further array 400 of exemplary control test data for oligomers of the 20 amino acids prepared in the same manner as described above in connection with FIG. 2, generated using the amino acid detection and identification apparatus 100. In this exemplary embodiment, each of the twenty amino acid oligomers so tested was constituted in a 0.25 molar polypeptide solution using undiluted dimethyl sulfoxide (DMSO) in order to generate the control solutions for testing. As in FIGS. 2 and 3, the left-most column of FIG. 4 shows row headings for the control test data array. The row headings identify and correspond to the metals, semiconductors and insulators on the bottom surfaces 138, 140, 142, 144, 146, 148, 150, 152 and 154 respectively of the amino acid detection and identification apparatus 100. The top-most row of FIG. 4 shows column headings for the control test data array. The column headings identify and correspond to the individual known amino acid oligomer solutions that were separately tested as reported in each column of the control test data array. The numerical data were again reported in units of $1\times10^3$ amino acid oligomer molecules per square micrometer. The control test data array shown in FIG. 4 is indicative of the relative concentrations of polypeptides bound to the indicated substantially inorganic surfaces when the test cells of the amino acid detection and identification apparatus 100 were subjected to known DMSO solutions of each individual polypeptide. In another embodiment, polypeptides were solubilized in a 1:5 DMSO:water solution at a 1 millimolar polypeptide concentration. Higher concentrations of DMSO can be beneficial in solubilizing polypeptides of Tyr, Phe and Leu.

Each of the data in the test cell data array 400 visually and numerically indicates the degree to which the designated polypeptide in each test bonded to the designated substantially inorganic surface. For example, data point 402 shows that a DMSO solution of polar-basic Arg polypeptide strongly bonded to $Si_3N_4$, as indicated both by the dark shading and the high numerical reading, $21\times10^3/\mu m^2$. Data point 403 shows, in contrast, that Thr polypeptide only lightly bonded to $Si_3N_4$, as indicated both by the light shading and the light reading, $2.1\times10^3/\mu m^2$. Further for example, data point 404 shows that a DMSO solution of polar-acidic Glu polypeptide firmly bonded to AlGaAs, as indicated both by the medium dark shading and the elevated numerical reading, $10\times10^3/\mu m^2$. Data point 405 shows, in contrast, that Asp polypeptide only lightly bonded to AlGaAs, as indicated both by the light shading and the light reading, $3.7\times10^3/\mu m^2$. Additionally for example, data point 406 shows that a DMSO solution of polar-neutral Thr polypeptide moderately bonded to Al, as indicated both by the grey shading and the moderate numerical reading, $4.4\times10^3/\mu m^2$. Data point 407 shows, in contrast, that Asn polypeptide only minimally bonded to Al, as indicated both by the lack of shading and the low numerical reading, $0.7\times10^3/\mu m^2$. Furthermore for example, data point 408 shows that a DMSO solution of non-polar neutral Cys polypeptide lightly bonded to $SiO_2$, as indicated both by the light shading and the light reading, $3.4\times10^3/\mu m^2$. Data point 409 shows, in contrast, that Met polypeptide moderately bonded to $SiO_2$, as indicated both by the moderate shading and the moderate reading, $4.6\times10^3/\mu m^2$. In addition, for example, data point 410 shows that a DMSO solution of non-polar neutral Met polypeptide minimally bonded to Au, as indicated both by the lack of shading and the low numerical reading, $0.9\times10^3/\mu m^2$.

FIG. 4 shows the strength of the bonding that results from exposure of each of the nine substantially inorganic surfaces separately to each of the twenty amino acid oligomers. As in the case of FIGS. 2 and 3, FIG. 4 shows that most of the strongest bonding reactions occurred with polar-acidic and polar-basic amino acid oligomers, and that the strongest bonding reactions involved the $Si_3N_4$, $SiO_2$, AlGaAs, and Al surfaces. However, each of the test cells did generate a numerical reading. In addition, each of the exemplary test data columns 412, 414, and 416 generated a different series of readings for the nine test surfaces. For example, Ala polypeptide in column 414 lightly bonded to $SiO_2$ and only minimally bonded to $Si_3N_4$, but Phe polypeptide in column 416 lightly bonded to both $SiO_2$ and $Si_3N_4$. These differential bonding patterns can be used to distinguish Ala from Phe. Further differential bonding patterns can be mapped from the FIG. 4 data and used to distinguish any two aqueous amino acid oligomers from each other in a likewise manner.

The preceding discussion in connection with FIGS. 1-4 has been directed to substantially inorganic surfaces made from the metals Pd, Au, Ti, Pt, and Al; the semiconductors GaAs, and AlGaAs; and the insulators $Si_3N_4$, $SiO_2$. It is to be understood, however, that other metals, semiconductors and insulators can be used in addition to or in substitution for one or more of the substantially inorganic surfaces addressed in FIGS. 1-4. In addition, alloys or mixtures of two or more such metals, semiconductors and insulators, and mixtures of one or more metals, semiconductors, and/or insulators can be used. Each of such materials will have its own characteristic pattern of bonding affinity for individual amino acids and polypeptides. These bonding affinities can be mapped in the same manner as discussed above in connection with FIGS. 1-4, and amino acid detection and identification apparatus can be constructed and used in the same manner.

In general, any metallic element or elements in the Periodic Table can be used, alone or together with other metals, semiconductors, and/or insulators, in a surface for selective amino acid or polypeptide bonding. In one embodiment, further metals that can be so used in addition to Pd, Au, Ti, Pt, and Al include: magnesium (Mg), calcium (Ca), zirconium (Zr), vanadium (V), tantalum (Ta), chromium (Cr), molybdenum (Mo), tungsten (W), manganese (Mn), iron (Fe), cobalt (Co), nickel (Ni), copper (Cu), silver (Ag), zinc (Zn), cadmium (Cd), gallium (Ga), indium (In), thalium (Tl), tin (Sn), and lead (Pb).

In general, any substantially inorganic compound semiconductors can be used, alone or together with other substantially inorganic compound semiconductors, metals, and/or insulators, in a surface for selective amino acid or polypeptide bonding. The semiconductors can be doped as desired, for example with elements that change the charge carrier mobility of such semiconductors. In one embodiment, further substantially inorganic compound semiconductors that can be so used, in addition to GaAs and AlGaAs, include: indium phosphide (InP), indium gallium arsenide (InGaAs), indium gallium phosphide (InGaAs), indium gallium arsenide phosphide (InGaAsP), indium aluminum gallium arsenide (InAlGaAs), gallium nitride (GaN), indium nitride (InN), aluminum nitride (AlN), aluminum gallium nitride (AlGaN), indium aluminum gallium nitride (InAlGaN), gallium antimonide (GaSb), indium antimonide (InSb), aluminum antimonide (AlSb), aluminum gallium antimonide (AlGaSb), indium aluminum gallium antimonide (InAlGaSb), indium arsenic antimonide (InAsSb), gallium aluminum antimonide (GaAlSb), indium gallium antimonide (InGaSb), and gallium arsenic antimonide (GaAsSb).

In general, any substantially inorganic insulator can be used, alone or together with other insulators, metals, and/or semiconductors, in a surface for selective amino acid or polypeptide bonding. In one embodiment, further substantially inorganic insulators that can be so used, in addition to $Si_3N_4$, and $SiO_2$, include: aluminum oxide ($Al_2O_3$), zinc oxide (ZnO), beryllium oxide (BeO), ferrite ($Fe_3O_4$), zirconium oxide ($ZrO_2$), boron carbide ($B_4C$), silicon carbide (SiC), magnesium diboride ($MgB_2$), and in general, metallic oxides, carbides, borides, nitrides, and sulfides.

FIGS. 2, 3 and 4 respectively employed water, HEPES diluted in water, and DMSO as a solvent for the polypeptides, forming solutions of such amino acid oligomers. Although the term "solution" is used throughout this discussion, it is to be understood that amino acid oligomers can alternatively be mobilized in other forms in fluids, such as, for example, dispersions, suspensions, gels, emulsions, and aerosols. Furthermore, water, HEPES diluted in water, and DMSO are exemplary solvents and fluid vehicles, and other solvents and fluid vehicles as suitable for the fluid mobilization of the polypeptides, proteins, or other amino acid-comprising compositions can also be used. Polar solvents such as water preferably dissolve polar-acidic, polar-basic and polar-neutral amino acids and polypeptides. Non-polar organic solvents preferentially dissolve non-polar neutral amino acids and polypeptides.

Figure 5:
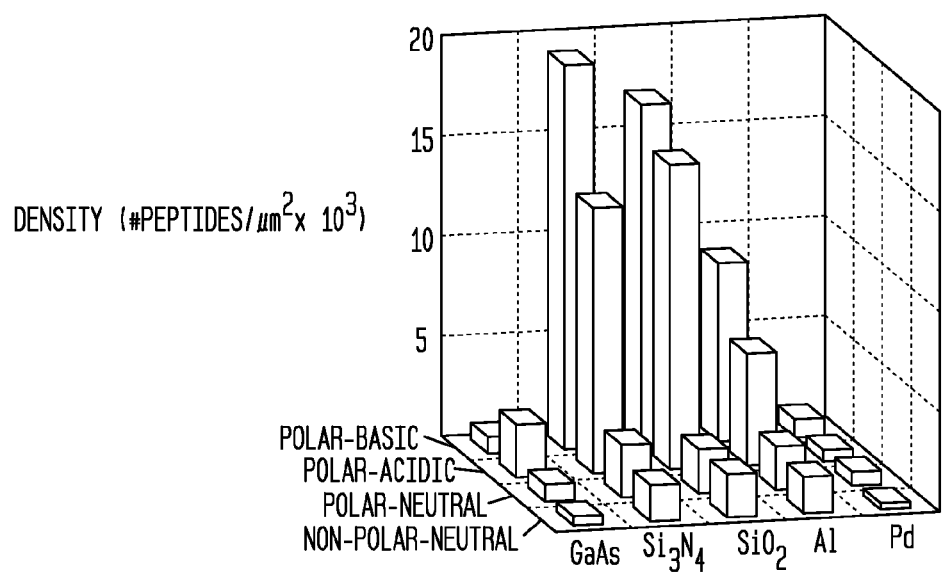
FIG. 5 shows data plotting the relative density of polar-basic, polar-acidic, polar-neutral and non-polar neutral polypeptides on various exemplary types of inorganic substrates.

FIG. 5 shows summary bar graph data based on the tests carried out to generate FIGS. 2-4, plotting the density on GaAs, $Si_3N_4$, $SiO_2$, Al and Pd surfaces, of equivalent bound polypeptides×$10^3$ per square micrometer ($\mu m^2$), as to each of the twenty amino acid oligomers. FIG. 5 shows that the strongest bonding interactions occurred when $Si_3N_4$ and $SiO_2$ surfaces were exposed to solutions of polar-basic polypeptides. FIG. 5 further shows that polar-acidic polypeptides generally adhered strongly to $Si_3N_4$ and $SiO_2$, although not as strongly as did the polar-basic polypeptides. FIG. 5 also shows that polar-basic and polar-acidic polypeptides generally adhered firmly to Al, although not as strongly as to $Si_3N_4$ and $SiO_2$. FIG. 5 additionally shows that polar-neutral and non-polar neutral polypeptides generally adhered moderately to $Si_3N_4$, $SiO_2$, and Al, although not as strongly as did polar-basic and polar-acidic polypeptides. FIG. 5 furthermore shows that all types of polypeptides, including polar-basic, polar-acidic, polar-neutral, and non-polar neutral polypeptides, generally adhered at least minimally or lightly to GaAs and Pd. FIG. 5 makes clear that the relative bonding affinity of polypeptides to the five exemplary substantially inorganic surfaces can be used in either a quantitative or relative qualitative manner together with known controls in order to identify particular polypeptides in solution.

Figure 6:
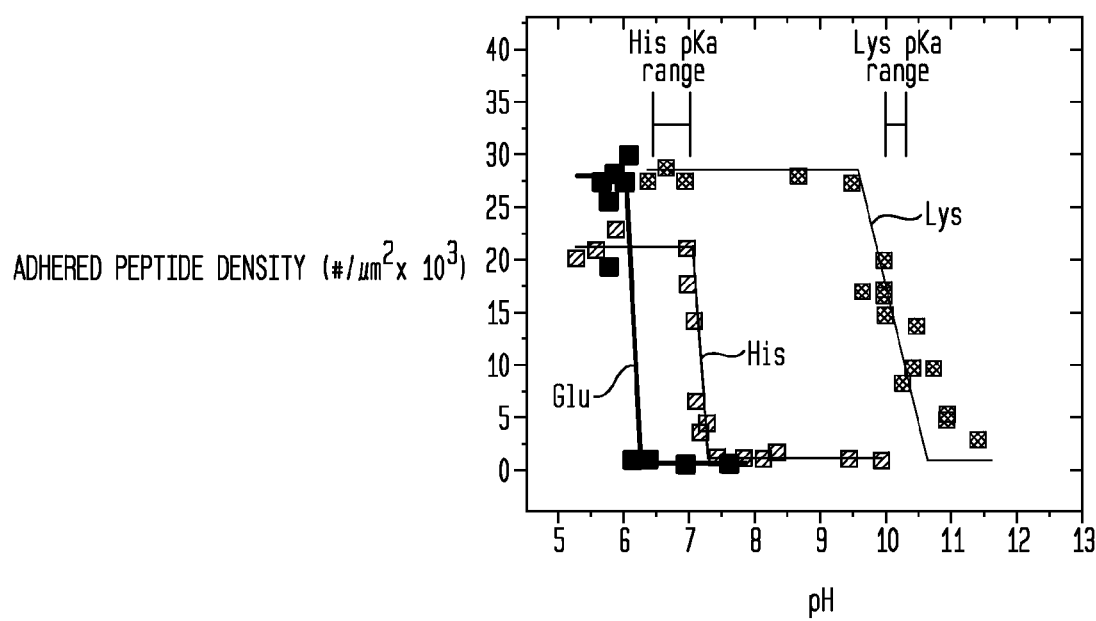
FIG. 6 shows data plotting the adhered density of bound polypeptides over a pH range.

FIG. 6 shows graphed data plotting on the y-axis the adhered density, on $Si_3N_4$ surfaces, of equivalent bound polypeptides×$10^3$ per $\mu m^2$ including Glu, His, and Lys, and on the x-axis a pH range of between about 5.5 and about 11.75. The pH can be increased, for example, by addition of $NH_4OH$. As to Glu, the density of equivalent bound polypeptides remained stable at about 27,000 per $\mu m^2$ of surface across a pH range of between about 5.5 and about 6.0; and gradually dropped to a minimal density that was then maintained at a pH above about 6.2. As to His, the density of equivalent bound polypeptides remained stable at about 22,000 per $\mu m^2$ of surface across a pH range of between about 5.2 and about 7.2; and gradually dropped to a minimal density that was then maintained at a pH above about 7.3. As to Lys, the density of equivalent bound polypeptides remained stable at about 28,000 per $\mu m^2$ of surface across a pH range of between about 6.2 and about 10.0; and gradually dropped to a minimal density then maintained at a pH above about 10.6. Similar effects can be demonstrated for the other polar-charged polypeptides, including polar-basic Arg and polar-acidic Asp. Ionization behavior of the polar-neutral polypeptides can also be used to affect the bonding affinity of these amino acid oligomers to substantially inorganic surfaces.

Figure 7:
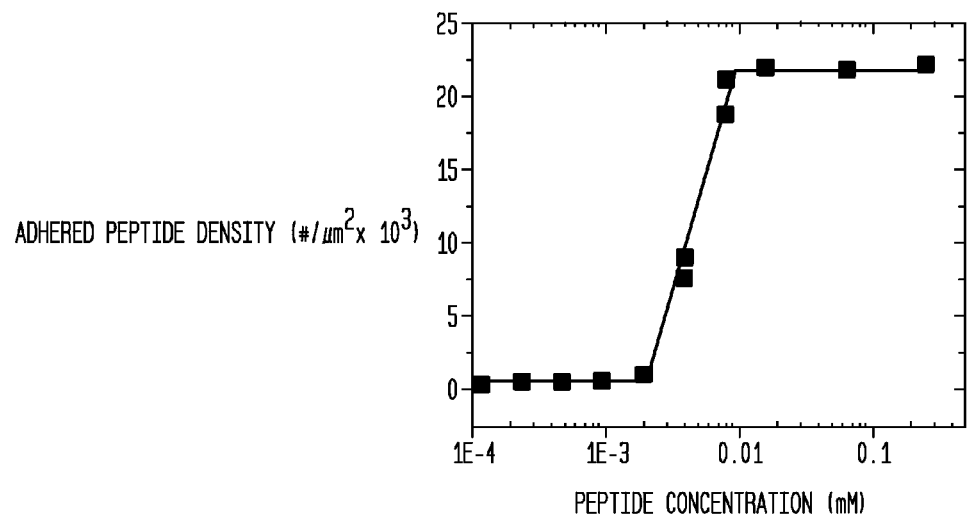
FIG. 7 shows data plotting the adhered density of bound polypeptides over a polypeptide concentration range.

FIG. 7 shows graphed data plotting on the y-axis the adhered density on $Si_3N_4$ surfaces, of equivalent bound His polypeptides×$10^3$ per $\mu m^2$, and on the x-axis a polypeptide concentration range of between about $1\times10^{-4}$ millimolar (thousandths of a mole of polypeptides per liter) (mM/l) and about $1\times10^{-1}$ mM/l. All concentrations are expressed as equivalent polypeptides in millimoles. FIG. 7 shows that for polypeptide solutions having amino acid oligomer concentrations of less than about $5\times10^{-3}$ mM/l, no appreciable bonding to the substantially inorganic surfaces occurs. Over a concentration range of between about $5\times10^{-3}$ mM/l and about $1\times10^{-2}$ mM/l, the density of adhered polypeptides steadily increases to about 24,000 equivalent bound polypeptides per $\mu m^2$, and this density is then maintained at higher polypeptide concentrations. Hence, FIG. 7 shows that a given substantially inorganic surface has a limited capacity for bonding polypeptides before saturation occurs.

Figure 8:
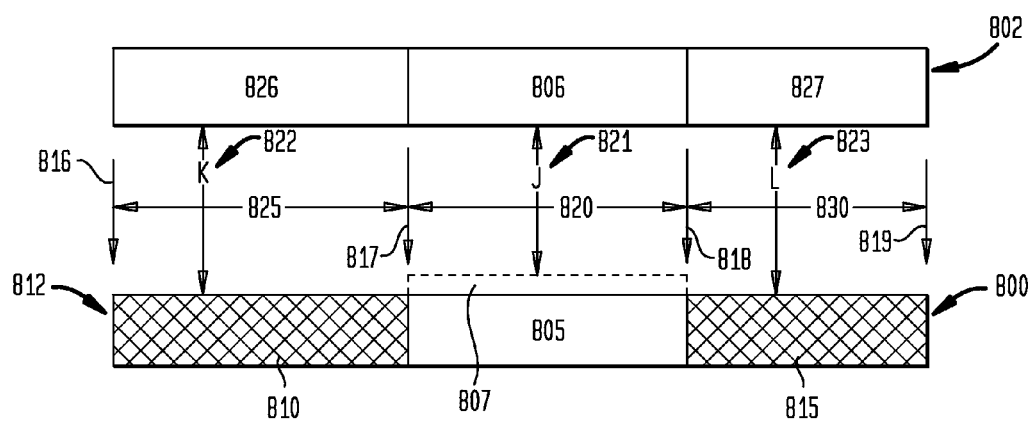
FIG. 8 shows a schematic side view of an embodiment of an amino acid detection and identification apparatus designed to selectively bond a particular polypeptide.

FIG. 8 shows a schematic side view of an embodiment of an amino acid detection and identification apparatus 800 designed to selectively bond a particular polypeptide, and shows such a polypeptide 802 suspended over the apparatus 800. In this embodiment, the apparatus 800 is designed to selectively bond a polypeptide comprising five (5) Asp molecules forming a polypeptide chain indicated at 806, the polypeptide having either three (3) or five (5) Leu molecules further extending the polypeptide chain at both ends. The amino acid detection and identification apparatus 800 comprises a midlayer of AlGaAs 805 interposed between two layers of GaAs 810 and 815. The GaAs layers 810 and 815 are visually distinguished by cross-hatching. The thickness of the AlGaAs midlayer 805 is about 1.9 nanometers (nm) as indicated by the double arrow 820. This thickness is less than or equal to the longitudinal length of the polypeptide consisting of five Asp molecules indicated at 806.

In one embodiment, the thickness of the GaAs layer 810 is about 1.7 nm as indicated by the double arrow 825. This thickness approximately matches or exceeds the longitudinal length of a polypeptide 826 consisting of three Leu molecules having end-bonded 5-carboxyfluorescein (5F-AM). Fluorescein is a fluorescent marker that enables detection of a bound polypeptide on the amino acid detection and identification apparatus 800. The 5F-AM marker extends the longitudinal length of the polypeptide itself. The thickness of the GaAs layer 815 is about 1.2 nm as indicated by the double arrow 830. This thickness approximately matches or slightly exceeds the longitudinal length of a polypeptide 827 consisting of three Leu molecules.

In an alternative embodiment, the thickness of the GaAs layer 810 is about 2.5 nm as indicated by the double arrow 825. This thickness approximately matches or exceeds the longitudinal length of a polypeptide consisting of five Leu molecules 826 having end-bonded 5F-AM. The thickness of the GaAs layer 815 is about 2 nm as indicated by the double arrow 830. This thickness approximately matches or exceeds the longitudinal length of a polypeptide 827 consisting of five Leu molecules.

In a further alternative embodiment, the AlGaAs midlayer 805 is extended to include region 807 indicated by a dotted line in FIG. 8. In this embodiment, the double arrow 821 indicates the distance j between the AlGaAs midlayer 805 and the polypeptide 806 comprising five (5) Asp molecules. Additionally in this embodiment, the double arrow 822 indicates the distance k between the GaAs layer 810 and the polypeptide consisting of five Leu molecules 826 having end-bonded 5F-AM. Further in this embodiment, the double arrow 823 indicates the distance l between the GaAs layer 815 and the polypeptide consisting of five Leu molecules 827 having an exposed —C—O—O—H end group. It can be seen that the distance j is less than the distances k and l. Stated otherwise, the region 807 constitutes a shelf on which the polypeptide 806 can rest. This shelf, and the greater distances k and l, provide extra space on which the polypeptides 826 and 827 can rest when the polypeptide 806 becomes bonded to region 807 of the AlGaAs midlayer 805. In this manner, the polypeptide 806 can more readily bond to the AlGaAs midlayer 805 without steric hindrance between the side groups of the Leu moieties and the GaAs layers 810 and 815.

In use, the amino acid detection and identification apparatus 800 is exposed to a solution of polypeptides. If any of the polypeptides include chains comprising Leu-Leu-Leu-Asp-Asp-Asp-Asp-Asp-Leu-Leu-Leu, or a similar polypeptide with two additional Leu molecules at each end of the chain, then such polypeptides will selectively bond to the amino acid detection and identification apparatus 800 having layers 805, 810 and 815 of the appropriate thickness discussed above. This bonding will occur in alignment with the arrows 816, 817, 818 and 819. Polypeptides having additional chain portions beyond the selectively bonded polypeptide will adhere only such selected polypeptide, leaving the other chain portions unbonded and trailing away from the apparatus 800. Selective polypeptide bonding can be detected, for example, by labeling the polypeptides with 5F-AM as discussed earlier. It will be understood that a given apparatus 800 may be capable of bonding more than one specific polypeptide sequence, as the various bonding surface materials often have bonding affinities for more than one amino acid.

The term "layer" as used throughout this specification is defined as a body of the subject material as applied over an adjoining surface, however such body is formed. A "layer" may have a non-uniform thickness, does not have to be completely continuous, and may be the result of any desired deposition process undertaken in one or more than one steps. Hence, a "layer" may also comprise multiple layers of the same or different materials, which may or may not interpenetrate each other, and which layers together are referred to as the "layer". There is no particular limitation on the thickness of a layer except as stated.

Figure 9:
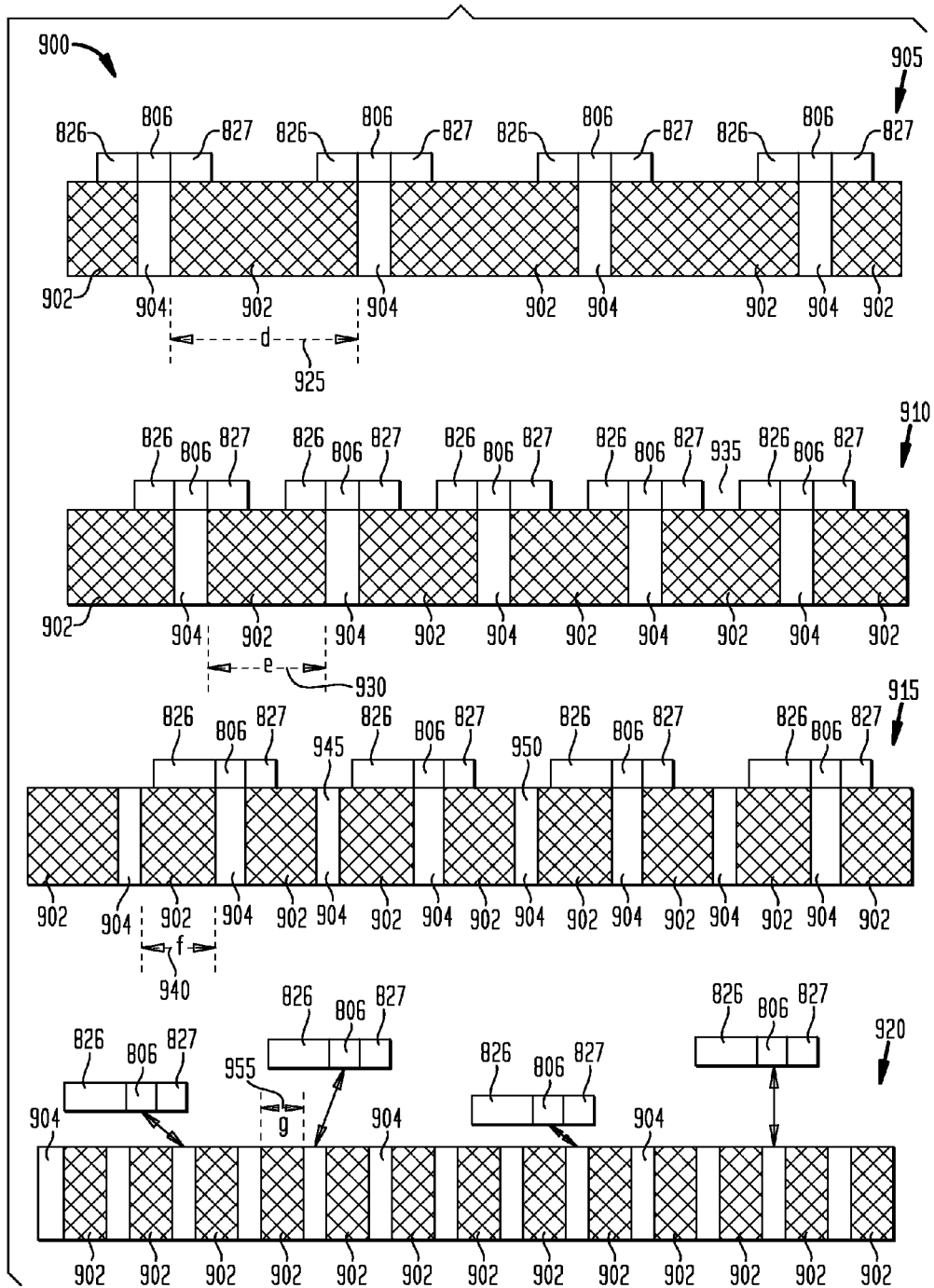
FIG. 9 shows schematic side views of a progressive series of four further amino acid detection and identification apparatus.

FIG. 9 schematically illustrates the importance of controlling the thicknesses of the layers in the amino acid detection and identification apparatus 800, in order to maximize the bonding potential for the polypeptide 802. The four images 900 represents schematic side views of a progressive series of amino acid detection and identification apparatus 905, 910, 915 and 920 similar to the amino acid detection and identification apparatus 800. Regions in the apparatus 905, 910, 915 and 920 distinguished by cross-hatching indicate GaAs layers 902, which are interposed by AlGaAs layers 904 without cross-hatching, similar to the structure of the apparatus 800 shown in FIG. 8. Each of the apparatus 905, 910, 915 and 920 has more than one bonding site for Leu-Leu-Leu-Asp-Asp-Asp-Asp-Asp-Leu-Leu-Leu, or for a similar polypeptide with two additional Leu molecules at each end of the chain. In the apparatus 905, the GaAs layers between any two adjacent polypeptide bonding sites have a thickness d, indicated by the double arrow 925. The thickness d is more than adequate to prevent steric interference between adjacently bonded polypeptides. In the apparatus 910, the GaAs layers between any two adjacent polypeptide bonding sites have a thickness e indicated by the double arrow 930 that is still adequate to prevent steric interference between adjacently bonded polypeptides, but some of the polypeptides nearly butt ends as at exemplary point 935. In the apparatus 915, the GaAs layers between any two adjacent polypeptide bonding sites have a thickness f indicated by the double arrow 940 that is too small to prevent steric interference between adjacent polypeptides at some of the potential bonding sites. Although some bonding can still occur, exemplary bonding sites 945 and 950 are sterically blocked, reducing the selective bonding capacity of the apparatus 915. In the apparatus 920, the distance between the AlGaAs layers of any two adjacent polypeptide bonding sites constitutes a thickness g indicated by the double arrow 955 that is too small to allow any selective bonding of polypeptides. At every intended bonding site, steric interference between adjacent AlGaAs midlayers prevents bonding of any polypeptides at any of the intended bonding sites. FIG. 9 illustrates the importance of designing and controlling the thicknesses of substantially inorganic layers for selective bonding of polypeptides in order to avoid decreased apparatus capacity or total failure due to steric hindrance factors. In a further alternative embodiment, the AlGaAs midlayers are extended in the same manner as discussed above in connection with the midlayer 805 and region 807 shown in FIG. 8.

Figure 10:
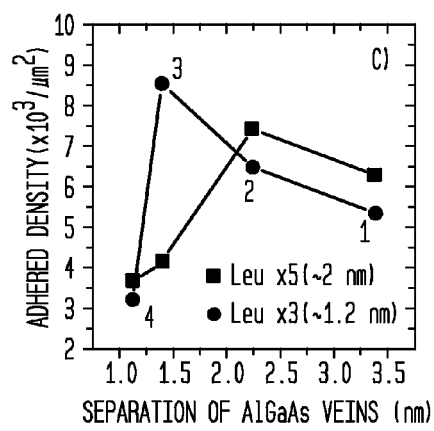
FIG. 10 shows data plotting the adhered density of bound polypeptides versus separation between mutually adjacent AlGaAs apparatus layers.

FIG. 10 plots data regarding the bonding of polypeptides on the amino acid detection and identification apparatus 905-920 shown in FIG. 9. The x-axis denotes the separations d, e, f and g, in nm, between mutually adjacent AlGaAs layers as shown in FIG. 9. The y-axis denotes the adhered density of equivalent bound polypeptides$\times 10^3$ per $\mu m^2$ on the amino acid detection and identification apparatus 905-920. The circular data plot trials in which the polypeptides applied to the amino acid detection and identification apparatus 905-920 had three Leu moieties on the polypeptide ends, each having an end-to-end length of about 1.2 nm. The square data plot trials in which the polypeptides applied to the amino acid detection and identification apparatus had five Leu moieties on the polypeptide ends, each having an end-to-end length of about 2 nm. In each case, the polypeptides were labeled at one end with 5F-AM. Referring first to the circular data points, the adhered density of Leu-Leu-Leu-Asp-Asp-Asp-Asp-Asp-Leu-Leu-Leu polypeptides steadily increased as the separation between the AlGaAs layers was reduced from about 3.4 nm to about 2.5 nm to about 1.4 nm, and then dramatically dropped as the separation was reduced to about 1.2 nm. The steady increase evident in the first three such data points indicates that there was no significant steric hindrance to polypeptide binding, while the packing density of binding sites became correspondingly greater. The sudden drop in polypeptide adhesion density at an AlGaAs layer separation of about 1.2 nm indicates that substantial steric hindrance to polypeptide bonding arose at this smaller layer separation. A similar pattern resulted in the square data points regarding the adhered density of Leu-Leu-Leu-Leu-Leu-Asp-Asp-Asp-Asp-Asp-Leu-Leu-Leu-Leu-Leu. In each case, the polypeptides were labeled at one end with 5F-AM. There, the polypeptide adhesion density increased as the AlGaAs layer separation was decreased from about 3.4 nm to about 2.5 nm. However, the adhesion density at an AlGaAs layer separation of about 1.4 nm was almost as low as that at a separation of about 1.2 nm. This result is consistent with the additional chain length of the polypeptides being selectively bonded in the square plotted data, because the additional polypeptide length caused steric hindrance to first arise at a greater AlGaAs layer separation. The results of the trials reported in FIG. 10 further illustrate the trend in bonding performance through the progression in amino acid detection and identification apparatus 905, 910, 915 and 920, as discussed in connection with FIG. 9.

Figure 11:
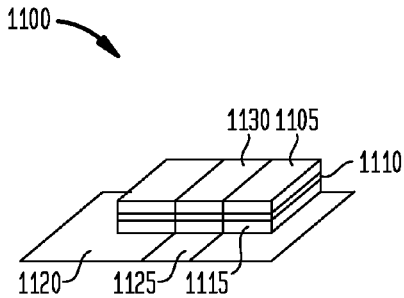
FIG. 11 shows a schematic perspective view of an embodiment of an amino acid detection and identification apparatus.

FIG. 11 shows a schematic perspective view of an embodiment of an amino acid detection and identification apparatus 1100. The apparatus 1100 comprises three sandwiched substantially inorganic layers 1105, 1110 and 1115, each of which may be independently selected from among the substantially inorganic metals, semiconductors and/or insulators and mixtures as earlier discussed. The optimal compositions of the layers 1105, 1110 and 1115 are determined by the polypeptide to be selectively bonded to and thus made detectable by the apparatus 1100. Referring back to FIG. 8, the selected polypeptide will then bond across layers 1105, 1110 and 1115 in the same manner as the exemplary Leu-Leu-Leu-Asp-Asp-Asp-Asp-Asp-Leu-Leu-Leu polypeptide bonded across layers 805, 810 and 815 discussed in connection with FIG. 8. One advantage of the structure of the apparatus 1100 is that the layers 1105, 1110 and 1115 can be successively built up on a non-bonding substrate 1120, and then etched to reveal layers with the selected bonding activity. In one embodiment, the thus exposed layers 1105, 1110 and 1115 are mutually flush so that a selected polypeptide will bond to all three layers. In another embodiment, one or more of the layers may be recessed or formed from a non-bonding material that serves as a spacing element rather than a bonding surface. In one embodiment, only the layer 1110 serves as a bonding surface for amino acids. In one modification of that embodiment, conductors 1125 and 1130 are in electrical communication with an external source for applying a voltage potential across the layer 1110. In this manner, a change in conductivity across the layer 1110 detected by the external voltage source is an indication of selective bonding of amino acids or polypeptides on the layer 1110. Although the exemplary apparatus 1100 comprises three layers 1105, 1110 and 1115, any desired number of bonding and/or spacing layers can be built up and exposed to selectively bond a desired polypeptide sequence. It will be understood that a given apparatus 1100 may be capable of bonding more than one specific polypeptide sequence, as the various surface materials often have bonding affinities for more than one amino acid. Apparatus can be designed to carry out the same operations with regard to macromolecules comprising amino acids, such as proteins.

Figure 12:
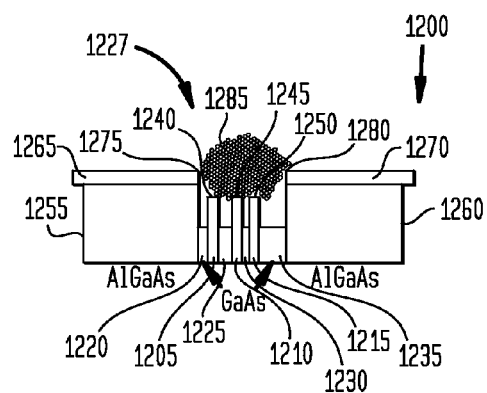
FIG. 12 shows a side view of an embodiment of another amino acid detection and identification apparatus.
Figure 13:
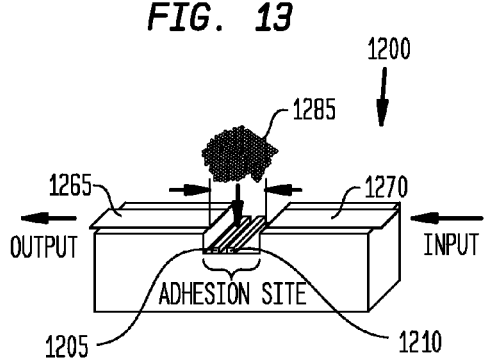
FIG. 13 shows a perspective view of the amino acid detection and identification apparatus in FIG. 12.

FIG. 12 shows an embodiment of an amino acid detection and identification apparatus 1200 which is suitable for the detection and identification of macromolecules comprising amino acids. The apparatus 1200 comprises AlGaAs surface site layers 1205, 1210, and 1215 interposed between GaAs interlayers 1220, 1225, 1230 and 1235. Distal site ends 1240, 1245 and 1250 of the AlGaAs surface site layers 1205, 1210, and 1215 extend beyond ends of the GaAs interlayers 1220, 1225, 1230 and 1235, forming a polypeptide bonding region 1227. All of the foregoing layers are sandwiched between AlGaAs support layers 1255 and 1260. Conductors 1265 and 1270 are provided on surfaces of the AlGaAs support layers 1255 and 1260 adjacent to the polypeptide bonding region 1227. The AlGaAs support layers 1255 and 1260 serve to position the conductors 1265 and 1270 adjacent to the polypeptide bonding region 1227, and to form the bonding region 1227 as a well for containing a test solution potentially containing a polypeptide macromolecule. A target polypeptide macromolecule 1285 having regions that selectively bond with AlGaAs, desirably located in precise alignment with the distal site ends 1240, 1245 and 1250, will then selectively bond on surfaces of the distal site ends to the apparatus 1200. The conductors 1265 and 1270 may be in electrical communication with an external voltage source for applying a potential across the bonding region 1227 between distal ends 1275 and 1280 of the conductors 1265 and 1270 respectively, for confirming the presence of a selectively bound polypeptide macromolecule on the apparatus 1200. A change in the conductivity across the bonding region 1227 is an indication of such presence. Alternatively, for example, the conductors 1265 and 1270 can be substituted by optical waveguides such as optical fibers or optical planar waveguides mutually aligned for light transmission and directing light across the bonding region 1227 so that a change in transmitted light through such optical waveguides is an indication of the selective bonding of a polypeptide macromolecule. In use, a solution potentially comprising the target polypeptide macromolecule is placed in the vicinity of the region 1227. If present in the solution, a target polypeptide macromolecule 1285 then selectively bonds to the apparatus 1200. FIG. 13 shows the same apparatus 1200 in perspective view. FIG. 13 shows the location of the conductors 1265 and 1270, and exemplary AlGaAs surface site layers 1205 and 1210.

Figure 14:
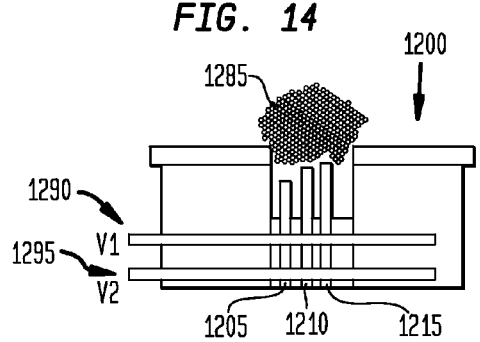
FIG. 14 shows a side view of an embodiment of an apparatus embodying modifications of the apparatus shown in FIG. 12.

FIG. 14 shows an apparatus 1400 embodying modifications of the apparatus 1200. The modifications enable the controlled and independent application of two different voltages to precisely located regions of a selectively bound polypeptide macromolecule 1285. In this embodiment, each of the AlGaAs surface site layers 1205, 1210 and 1215 is formed from an electrical conductor or semiconductor having a charge carrier mobility, optionally p-doped or n-doped. The layers 1205 and 1215 are in electrical contact with conductor 1290, and the layer 1210 is in electrical contact with conductor 1295. Accordingly, a first voltage V1 can be applied to the layers 1205 and 1215 through conductor 1290, and a second voltage V2 can independently be applied to the layer 1210 through conductor 1295. Application of such voltages can be used to modulate the binding of the target polypeptide macromolecule as a further aid in its detection and/or identification.

Figure 15:
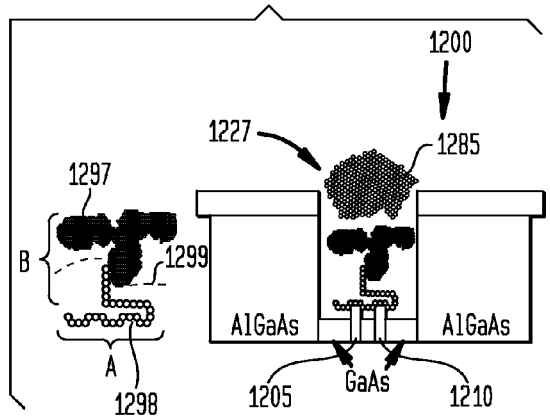
FIG. 15 shows an application of the apparatus shown in FIG. 12 for the detection and identification of a target polypeptide macromolecule in which an antibody for the macromolecule is employed.

FIG. 15 shows an application of the apparatus 1200 for the detection and identification of a target polypeptide macromolecule 1285, employing an antibody to the target polypeptide macromolecule. In this embodiment, an antibody 1297 is provided having specific binding affinity for a target polypeptide macromolecule 1285 constituting an antigen. The antibody 1297 is anchored within the region 1227 by a polypeptide chain 1298. The polypeptide chain 1298 is selectively bonded to exemplary layers 1205 and 1210. The polypeptide chain 1298 is bonded to the antibody 1297 at their interface as indicated by the dotted line 1299. The polypeptide chain 1298 comprises a polypeptide subregion having a specific binding affinity for the exemplary layers 1205 and 1210. In use, the antibody is selectively bonded to the region 1227 by the layers 1205 and 1210. A solution that potentially includes the target polypeptide macromolecule 1285 is then placed in the vicinity of the region 1227. If the target polypeptide macromolecule 1285 is present in the solution, a target macromolecule 1285 selectively bonds to the antibody 1297 secured to the region 1227 of the apparatus 1200.

FIG. 16 shows an embodiment of an additional amino acid detection and identification apparatus 1600 which is suitable for the selective detection and identification of an amino acid, polypeptide, or macromolecule comprising amino acids. The apparatus 1600 comprises an electrically conductive comb 1602 comprising tines 1604, 1606, 1608, 1610, 1612, 1614, 1616 and 1618. The apparatus 1600 further comprises an electrically conductive comb 1603 comprising tines 1605, 1607, 1609, 1611, 1613, 1615, 1617, 1619, and 1621. The tines 1604-1618 of the comb 1602 are interlaced with and separated by small distances from the tines 1605-1621 of the comb 1603. Pad 1630 is in electrical communication with the comb 1602; and pad 1632 is in electrical communication with the comb 1603. The pads provide a surface of adequate size for the application of an externally generated voltage potential, such as by touching electrically charged probes to the pads. The combs 1602 and 1603 are made from two independently selected electrically conductive materials comprising substantially inorganic metals, semiconductors and/or insulators as earlier discussed. Although the combs are not fabricated solely from insulators, they can be fabricated from materials comprising insulators together with metals and/or semiconductors. The combs 1602 and 1603 are separated by substrate 1634. The electrical conductivity of the substrate 1634 is adequately reduced relative to that of the combs 1602 and 1603 such that a voltage potential across a gap between the combs 1602 and 1603 can be generated. The small distances between the tines of the combs are then designed and precisely fabricated in a manner analogous to the manner in which the AlGaAs layer 805 is prepared as discussed above in connection with FIGS. 8-10. In use, a solution of an amino acid, polypeptide, or macromolecule comprising amino acids is applied to the tines 1604-1621 of the combs 1602 and 1603 and to the gap between them across the substrate 1634. In one embodiment, the minimum path length across the gap is within a range of between about 200 Angstroms (Å) and about 2000 Å. Target amino acids, polypeptides, or macromolecules with a bonding affinity for the alternating surfaces of the tines in combs 1602 and 1603 will selectively bond to the apparatus 1600. Following removal of the solution of unbonded amino acids, polypeptides or other macromolecules, the charge carrier conductivity of the combs 1602 and 1603 can be tested. A change in conductivity indicates bonding of the amino acids, polypeptides, or macromolecules.

FIG. 17 shows an embodiment of a method 1700 for making the amino acid detection and identification apparatus 100 as discussed above in connection with FIGS. 1-4. In a series of steps 1705 and 1710, the amino acid detection and identification apparatus 100 is fabricated. In step 1705, a substrate is provided for a column of test cells 102, 104, 106, 108, 110, 112, 114, 116 and 118. The substrate may be made from any material suitable for the fabrication of a supportive base for test surfaces, such as a polymer, metal, or ceramic. A raised outer boundary wall 120 is provided on the substrate that is capable of containing a sample of an amino acid or polypeptide solution. Further raised boundary walls 122, 124, 126, 128, 130, 132, 134 and 136 are provided on the substrate, defining and mutually separating the test cells 102-118. The cells 102-118 define exposed and mutually separated portions of the substrate. In step 1710, bottom surfaces 138, 140, 142, 144, 146, 148, 150, 152 and 154, respectively, are provided on each of the exposed and mutually separated portions of the substrate. The bottom surfaces 138-154 each independently comprise a selected inorganic metal, semiconductor, and/or insulator surface that selectively adheres amino acids. The bottom surfaces 138-154 can each be prepared on the substrate using any suitable process, such as evaporation, vapor deposition or electrodeposition. In this embodiment, the metals Pd, Au, Ti, Pt, and Al; the semiconductors GaAs and AlGaAs; and the insulators $Si_3N_4$ and $SiO_2$, are used. Accordingly, the bottom surfaces 138, 140, 142, 144, 146, 148, 150, 152 and 154 respectively comprise: GaAs, $Si_3N_4$, $SiO_2$, AlGaAs, Al, Pt, Ti, Au, and Pd. In one embodiment, oxides naturally formed on the metal surfaces such as aluminum oxide are not removed.

FIG. 18 further shows steps 1805, 1810, 1815, 1820, and 1825 of a method 1800 for using the apparatus 100 for detection and identification of a polypeptide 1830 in a fluid. In step 1805, a selected control polypeptide composition is deposited in each of the test cells 102, 104, 106, 108, 110, 112, 114, 116 and 118 of the amino acid detection and identification apparatus 100. As earlier discussed, the polypeptide compositions can be mobilized in any form of fluid, such as, for example, solutions, dispersions, suspensions, gels, emulsions, and aerosols. Furthermore, solvents and fluid vehicles other than water, HEPES diluted in water, and DMSO can be used. In step 1810, first data are recorded as to selective affinity of each selected test surface for each control polypeptide composition. A separate apparatus 100 may be used to carry out each control test, or an apparatus 100 can be chemically treated to remove any bound polypeptides and reused. In step 1815, an unknown polypeptide composition is deposited on an amino acid detection and identification apparatus 100. In step 1820, second data are recorded as to selective affinity of each selected test surface for the unknown polypeptide composition. In step 1825, the second data are correlated with the first data to detect and identify the unknown polypeptide composition 1830. It is to be understood that the compositions can comprise more than one polypeptide or may have been previously treated, e.g., by chromatography or electrophoresis, to isolate a single polypeptide for identification.

FIG. 19 shows an embodiment of a method 1900 for making amino acid detection and identification apparatus 800 as discussed above in connection with FIGS. 8 and 9. In a series of steps 1905, 1910, 1915, and 1920, the amino acid detection and identification apparatus 800 is fabricated. In step 1905, a first plurality of surface sites 810 are provided, each comprising a first substantially inorganic surface selected from the group consisting of metals, semiconductors, insulators, and mixtures, each of said first surfaces having selective affinity for bonding of a portion of a polypeptide. In step 1910, a second plurality of surface sites 805 are provided, each comprising a second substantially inorganic surface selected from the group consisting of metals, semiconductors, insulators, and mixtures, each of said second surfaces having selective affinity for bonding of a portion of a polypeptide. In another embodiment, in step 1915, a third plurality of surface sites 815 are provided, each comprising a third substantially inorganic surface, the second plurality of surface sites 805 interposed between and adjacent to the first and third pluralities 810 and 815, and having a thickness for spacing the first and third pluralities of surface sites apart by a distance suitable for selectively bonding another portion of a polypeptide to the second plurality of surface sites 805. The first, second and third pluralities of surface sites 805, 810 and 815 can be fabricated, for example, as successively deposited layers on a substrate, not shown, which can for example be interfaced with the side 812 of the layer 810. In one embodiment, in step 1920 each of the first plurality of surface sites 810 is provided with a first substantially inorganic surface extending for a distance away from the adjacent second surface site 805, the distance being suitable for selectively bonding a portion of a polypeptide to each of the first plurality of surface sites 810.

The deposition steps in FIG. 19 can be carried out, for example, using a vapor deposition process such as molecular beam epitaxy (MBE). Other vapor deposition techniques, such as plasma enhanced chemical vapor deposition (PECVD) can also be used. The AlGaAs layers can be selectively exposed using an etch of $H_2O_2/NH_4OH$ followed by cleaning with an oxygen plasma. In one embodiment, the AlGaAs surface site layers had thicknesses of about 0.85 nm and the GaAs interlayers had thicknesses within a range of between about 1.15 nm and about 5.94 nm. To achieve a total device thickness of about 10 microns, roughly 3,000 alternating periods of GaAs and AlGaAs could be used. Extensive pauses between depositions of the alternating periods are advantageously used. After fabrication of the device periods, the layering is exposed by cleavage in air. A wet etch of $H_2O_2/NH_4OH$ (500:1) is then applied, followed by a water rinse and nitrogen drying. The wet etch is selective to GaAs versus AlGaAs by a factor of at least about 300:1, thus leaving a set of veins of AlGaAs surface sites protruding above a background of GaAs. Exposure to water modifies the adhesive properties of AlGaAs when compared to washes only in organic solvents. In an alternative embodiment, AlGaAs is selectively applied to a GaAs substrate using lithographic masking techniques to form the veins. In another embodiment, the Al content of AlGaAs is used to control the etching. As the Al content is reduced, the etching activity on the AlGaAs itself increases, enabling reduction of the AlGaAs thickness.

In one embodiment, $Si_3N_4$ and $SiO_2$ were deposited as 30 nanometer (nm) thick films using plasma enhanced chemical vapor deposition (PECVD). Photolithography was used to produce patterns on a micron-length scale, and dry reactive ion etching (RIE) of the $Si_3N_4$ and $SiO_2$ was accomplished with $CF_4$ and $CH_3F$ respectively to reveal the underlying GaAs. The metals Au, Pd, Pt, Ti and Al were deposited using electron beam- or thermal-evaporation. The apparatus 800 were exposed to a four (4) minute oxygen plasma etch as a cleaning step.

FIG. 20 further shows steps 2005, 2010 and 2015 of a method 2000 for using the apparatus 800 for detection and identification of a polypeptide 2020 in a fluid. Referring to FIG. 20, the amino acid detection and identification apparatus 800 is first calibrated with known polypeptides in step 2005. Next, data are recorded in step 2010 as to selective affinity of the apparatus 800 for an unknown polypeptide composition. In step 2015, the experimental data are correlated with the calibration data to detect and identify the polypeptide 2020.

FIG. 21 shows an embodiment of a method 2100 for making amino acid detection and identification apparatus 1200 as discussed above in connection with FIGS. 12, 13 and 14. In a series of steps 2105, 2110 and 2115, the amino acid detection and identification apparatus 1200 is fabricated. In step 2105, a first surface site layer 1205 is provided, formed from a first substantially inorganic composition selected from the group consisting of metals, semiconductors, insulators, and mixtures, said first surface site layer having selective affinity for bonding of a polypeptide. In step 2110, a plurality of interlayers 1220 and 1225 are provided, between which the first surface site layer 1205 is interposed. In step 2115, the first surface site layer 1205 is provided with a distal site end 1240 extending away from the interlayers 1220 and 1225, the distal site end 1240 comprising a first surface having selective affinity for bonding of a polypeptide. In one embodiment, steps 2105, 2110 and 2115 are repeated for the fabrication of a second surface site layer 1210. In another embodiment, the first and second surface site layers 1205 and 1210 and their respective interlayers are interposed between first and second support layers 1255 and 1260 in step 2120, and first and second conductors 1265 and 1270 are provided on said first and second support layers in step 2125 including first and second distal conductor ends 1275 and 1280 mutually aligned at a gap adjacent to said first and second surface sites. Referring back to FIG. 14, in an alternative embodiment each of the AlGaAs surface site layers 1205, 1210 and 1215 is formed from an electrical conductor or semiconductor, optionally p-doped or n-doped. The layers 1205 and 1215 are then suitably fabricated by semiconductor masking, deposition and etching steps so as to be placed in electrical contact with subsequently-formed conductor 1290. Similarly, the layer 1210 is suitably fabricated by semiconductor masking, deposition and etching steps so as to be placed in electrical contact with conductor 1295. For example, in step 2130 metals suitable for forming conductors compatible with the n- and p-doped semiconductors used in making a particular device can be diffused through the various layers to make selective contact with the layers 1205, 1210 and 1215.

FIG. 22 further shows steps 2205, 2210, 2215, 2220, 2225 and 2230 for using the apparatus 1200 for detection and identification of a polypeptide macromolecule 1285 in a fluid. In step 2205 a control polypeptide macromolecule is deposited at the first surface site 1240. In step 2210, first data are recorded as to selective affinity of the first surface site 1240 for the control polypeptide macromolecule. In step 2215, the apparatus 1200 is regenerated by removal of any bound control polypeptide, or an additional amino acid detection and identification apparatus is provided for testing of a fluid comprising an unknown polypeptide macromolecule. In step 2220, an unknown polypeptide macromolecule is deposited at the first surface site 1240. In step 2225, second data are recorded as to selective affinity of the first surface site 1240 for the unknown polypeptide macromolecule. In step 2230, second data are correlated with first data to detect and identify the polypeptide macromolecule 2235. In an embodiment where the conductors 1290 and 1295 are provided, an external bias can be provided in electrical communication with such conductors, capable of applying a voltage potential across the region 1227.

In one embodiment, the specificity of an apparatus 1200 for bonding and thus detecting a specific polypeptide macromolecule is tested by first producing polypeptides having active regions consistent with the active regions of the macromolecule considered as bonding sites, which are fluorescently labeled. The capability of the apparatus 1200 to bond such polypeptides is then tested. When a suitable spatial arrangement of bonding sites in the apparatus 1200 for bonding such polypeptides is found, then polypeptides of increased size emulating the local region of the target macromolecule near the active bonding sites are generated and tested for bonding capability. Once acceptable bonding is attained, then bonding of a known sample solution of the target macromolecule is tested. Atomic force microscopy is then used to detect the bonding of the target macromolecule, and fluorescent labeling is discontinued. The specificity of the apparatus 1200 can then be assessed by testing adhesion of known false positive producing proteins. The structure of the apparatus 1200 is then adjusted to sterically hinder bonding of such false positive producing proteins. In embodiments where conductors 1290 and 1295 are provided, the bonding capabilities of the apparatus 1200 can be adjusted by modulating voltage biases applied to such conductors in order to improve the specific bonding affinity of the apparatus 1200 for a target polypeptide macromolecule. Certain conductor compositions enable charge carrier mobility predominantly in either p-doped or n-doped semiconductors. The specificity of this conductivity can be further utilized to fabricate apparatus 1200 in which external voltage biases applied to the conductors 1290 and 1295 can be used to selectively modify the bonding characteristics of the apparatus.

FIG. 23 shows an embodiment of a method 2300 for making amino acid detection and identification apparatus 1600 as discussed above in connection with FIG. 16. In a series of steps 2305, 2310, 2315 and 2320, the amino acid detection and identification apparatus 1600 is fabricated. In step 2305, a substrate 1634 formed from an electrically insulating composition is provided. In step 2310, a first comb 1602 is formed on the substrate 1634 comprising first tines 1604, 1606, 1608, 1610, 1612, 1614, 1616 and 1618 formed from a first substantially inorganic composition selected from the group consisting of metals, semiconductors, insulators, and mixtures, said first tines having selective affinity for bonding of a polypeptide. In step 2315, a second comb 1603 comprising second tines 1605, 1607, 1609, 1611, 1613, 1615, 1617, 1619 and 1621 is formed from a second substantially inorganic composition selected from the group consisting of metals, semiconductors, insulators, and mixtures, said second tines having selective affinity for bonding of a polypeptide. In step 2320, desirably carried out simultaneously with steps 2310 and 2315, the first and second combs 1602 and 1603 are positioned on the substrate 1634 with their respective tines placed in mutually interwoven relationships at a spaced apart distance that is suitable for traversal by a polypeptide bonded to, or by multiple polypeptides located between and separately bonded to, mutually adjacent first and second tines. The resulting amino acid detection and identification apparatus 1600 can be used in a manner similar to that discussed in connection with the other apparatus above.

It will be recognized that the present teachings may be adapted to a variety of contexts consistent with this disclosure and the claims that follow. The apparatus disclosed herein may be designed for selective bonding affinity with any amino acid-comprising molecules, ranging from amino acids to macromolecules such as proteins. The substantially inorganic materials for fabrication of surfaces having bonding affinity for such molecules broadly include metals, semiconductors and/or insulators.

We claim:

1. An apparatus, comprising:
  a molecule identification device, including:
    a substrate;
    a first electrically-conductive comb, the first comb having a first back and a first plurality of tines spaced apart along the first back, each of the tines of the first plurality being formed of a composition that includes an inorganic electrical conductor or semiconductor and being located on the substrate;
    a second electrically-conductive comb, the second comb having a second back and a second plurality of tines spaced apart along the second back, each of the tines of the second plurality being formed of a composition that includes an inorganic electrical conductor or semiconductor and being located on the substrate, the tines of the first plurality being interlaced between the tines of the second plurality, wherein the interlaced tines are separated by gaps; and
    a first electrically-conductive pad located on the substrate and being electrically connected with the first comb, and a second electrically-conductive pad located on the substrate and being electrically connected with the second comb, wherein the first and second pads are capable of applying an externally-generated voltage across the combs, and wherein the apparatus is configured for selective identification of an amino acid-containing polypeptide or macromolecule.

2. The apparatus of claim 1, further including an external voltage source configured for applying the voltage across the combs.

3. The apparatus of claim 2, wherein the external voltage source is configured for detecting a change in an electrical conductivity across the combs, and wherein the apparatus is configured for utilizing the change in the electrical conductivity in the selective identification.

4. The apparatus of claim 1, wherein each of the gaps has a minimum length between one of the tines of the first plurality and an adjacent one of the tines of the second plurality, and wherein each of the minimum lengths is within a range of between about 200 Angstroms and about 2,000 Angstroms.

5. The apparatus of claim 1, wherein each of the gaps has a minimum length between one of the tines of the first plurality and an adjacent one of the tines of the second plurality, and wherein each of the minimum lengths is configured for selective bonding of an amino acid-containing polypeptide or macromolecule onto one of the tines of the first plurality and an adjacent one of the tines of the second plurality.

6. The apparatus of claim 1, wherein the compositions of some of the tines of the first plurality are different than the compositions of some of the tines of the second plurality.

7. The apparatus of claim 1, wherein the compositions of some of the tines of the first and second pluralities include a metal oxide, a metal carbide, a metal boride, a metal nitride, or a metal sulfide.

8. The apparatus of claim 1, wherein the compositions of some of the tines of the first and second pluralities include silicon nitride, silicon dioxide, aluminum oxide, zinc oxide, beryllium oxide, ferrite, zirconium oxide, boron carbide, silicon carbide, or magnesium diboride.

9. The apparatus of claim 1, wherein the compositions of some of the tines of the first and second pluralities include a semiconductor.

10. The apparatus of claim 1, wherein the compositions of some of the tines of the first and second pluralities include a group III-V semiconductor.

11. The apparatus of claim 1, wherein the compositions of some of the tines of the first and second pluralities include gallium arsenide, aluminum gallium arsenide, indium phosphide, indium gallium arsenide, indium gallium phosphide, indium gallium arsenide phosphide, indium aluminum gallium arsenide, gallium nitride, indium nitride, aluminum nitride, aluminum gallium nitride, indium aluminum gallium nitride, gallium antimonide, indium antimonide, aluminum antimonide, aluminum gallium antimonide, indium aluminum gallium antimonide, indium arsenic antimonide, gallium aluminum antimonide, indium gallium antimonide, or gallium arsenic antimonide.

12. The apparatus of claim 1, wherein the compositions of some of the tines of the first and second pluralities include palladium, gold, titanium, platinum, aluminum, magnesium, calcium, zirconium, vanadium, tantalum, chromium, molybdenum, tungsten, manganese, iron, cobalt, nickel, copper, silver, zinc, cadmium, gallium, indium, thalium, tin, or lead.

* * * * *